United States Patent
Kim et al.

(10) Patent No.: US 8,691,522 B2
(45) Date of Patent: Apr. 8, 2014

(54) COMPOSITION COMPRISING EXTRACELLULAR MEMBRANE VESICLES DERIVED FROM INDOOR AIR, AND USE THEREOF

(75) Inventors: Yoon Keun Kim, Pohang-si (KR); Yong Song Gho, Pohang-si (KR); Yu Sun Kim, Pohang-si (KR); Eun Jeong Choi, Busan (KR); Sung Wook Hong, Sokcho-si (KR); Eun Young Lee, Pohang-si (KR); Bok Sil Hong, Pohang-si (KR); Jun Pyo Choi, Pohang-si (KR); Young Koo Ji, Seongnam-si (KR)

(73) Assignee: Aeon Medix Inc., Pohang-si, Gyeongsangbuk-do (KR)

( * ) Notice: Subject to any disclaimer, the term of this patent is extended or adjusted under 35 U.S.C. 154(b) by 0 days.

(21) Appl. No.: 13/499,653

(22) PCT Filed: Aug. 5, 2010

(86) PCT No.: PCT/KR2010/005125
§ 371 (c)(1),
(2), (4) Date: Mar. 30, 2012

(87) PCT Pub. No.: WO2011/043538
PCT Pub. Date: Apr. 14, 2011

(65) Prior Publication Data
US 2012/0192295 A1    Jul. 26, 2012

(30) Foreign Application Priority Data
Oct. 8, 2009  (KR) ............ 10-2009-0095620

(51) Int. Cl.
*C12Q 1/04* (2006.01)
(52) U.S. Cl.
USPC ............................................ 435/34
(58) Field of Classification Search
None
See application file for complete search history.

(56) References Cited

U.S. PATENT DOCUMENTS

| 2005/0013831 | A1 | 1/2005 | Foster et al. |
| 2007/0154495 | A1 | 7/2007 | Gorrimge et al. |
| 2010/0260805 | A1 | 10/2010 | Hafner et al. |
| 2010/0298239 | A1 | 11/2010 | Hafner et al. |

FOREIGN PATENT DOCUMENTS

| JP | 2005514388 A | 5/2005 |
| JP | 2007508537 A | 4/2007 |
| WO | 03/051379 A1 | 6/2003 |
| WO | 2005/035733 A2 | 4/2005 |
| WO | 2009022156 A2 | 2/2009 |

OTHER PUBLICATIONS

Lee et al. (Proteomics, 7:3143-3453, 2007).*
Shoemaker et al., "Intranasal Delivery of Group B Meningococcal Native Outer Membrane Vesicle Vaccine Induces Local Mucosal and Serum Bactericidal Antibody Responses in Rabbits", Infection and Immunity, Aug. 2005, vol. 73, No. 8, pp. 5031-5038.
Murphy et al., "Construction of a Mutant and Characterization of the Role of the Vaccine Antigen P6 in Outer Membrane Integrity of Nontypeable Haemophilus influenzae", Infection and Immunity, Sep. 2006, vol. 74, No. 9, pp. 5169-5176.
Sanjay Sethi, M.D., et al.,"New Strains of Bacteria and Exacerbations of Chronic Obstructive Pulmonary Disease", The New England Journal of Medicine, Aug. 15, 2002, vol. 347, No. 7, pp. 465-471.
Nicola et al., "Lipohilic Dye Staining of *Cryptococcus neoformans* Extracellular Vesicles and Capsule", Eukaryotic Cell, Sep. 2009, vol. 8, No. 9, pp. 1373-1380.
Lee et al., "Proteomics in Enterotoxigenic *Staphylococcus aureus* Membrane Vesicles", KHUPO 9th Annual International Proteomics Conference, Mar. 25-27, 2009, p. 88.
International Search Report dated Apr. 27, 2011 of PCT/KR2010/005125 which is the parent application, English translation is enclosed—17 pages.
György, et al., "Membrane vesicles, current state-of-the-art: emerging role of extracellular vesicles", CMLS Cellular and Molecular Life Science, vol. 68, No. 16, 2011, pp. 2667-2688.
Kuehn, et al., "Bacterial outer membrane vesicles and the host-pathogen interaction", Genes and Development, Cold Spring Harbor Laboratory Press, vol. 19, No. 22, 2005, pp. 2645-2655.
Kim, et al., "Extracellular vesicles, especially derived from Gram-negative bacteria, in indoor dust induce neutrophilic pulmonary inflammation associated with both Th1 and Th17 cell response", Clinical & Experimental Allegy, vol. 43, No. 4, 2013, pp. 443-454.
Supplementary European Search Report dated Jul. 23, 2013 of the corresponding European Patent Application No. 10822183.9.

* cited by examiner

*Primary Examiner* — Brian J Gangle
(74) *Attorney, Agent, or Firm* — Knobbe, Martens, Olson & Bear, LLP

(57) ABSTRACT

The present application relates to a composition comprising extracellular membrane vesicles derived from indoor air. In addition, the present application provides a method for diagnosing, preventing and/or treating an inflammatory respiratory disease, lung cancer and the like using the extracellular membrane vesicles. In detail, the present application involves injecting extracellular membrane vesicles present in indoor air into an animal in order to prepare an animal respiratory disease model, and enables the search and/or discovery of drug candidates for preventing or treating respiratory diseases using the animal model. The present application provides a vaccine for preventing and/or treating respiratory diseases, to a method for diagnosing substances causing respiratory diseases, and to a method for inhibiting the activities of extracellular membrane vesicles in indoor air or removing the extracellular membrane vesicles from indoor air so as to prevent the occurrence and exacerbation of respiratory diseases.

10 Claims, 38 Drawing Sheets

Scale bar = 0.5 µm

Scale bar = 0.2 µm

FIG. 21

- Mite 20 g : washing with filtered PBS (4℃, 24h)
  ↓
- high speed centrifugation (4℃, 10000 g, 15 min)
  ↓
- high speed centrifugation (4℃, 10000 g, 15 min)
  ↓
- 0.22um filtration
  ↓
- ultra centrifugation (4℃, 150000 g, 3h)
  ↓
- pelleting
  ↓
- optiprep
  ↓
- ultra centrifugation (4℃, 100000 g, 2h)
  ↓
- protein level evaluation & TEM

COMPOSITION COMPRISING EXTRACELLULAR MEMBRANE VESICLES DERIVED FROM INDOOR AIR, AND USE THEREOF

TECHNICAL FIELD

The present invention relates to a composition comprising extracellular membrane vesicles derived from indoor air, and a method for the diagnosis, prophylaxis and/or therapy of inflammatory respiratory diseases, using the same.

BACKGROUND ART

Indoor air quality is a term which refers to the air quality within and around buildings and structures, especially as it relates to the health and comfort of building occupants. Indoor air quality can be affected by gases, particulates, biological contaminants, bacteria or any mass or energy stressor that can induce adverse health conditions. Representatives among the gases are volatile organic chemicals (VOC) including benzene, formaldehyde, pentachlorobenzene, toluene, xylene and styrene, and radon. Biological contaminants of indoor air may include bacteria, mould, viruses, house dust mites, cockroaches, cat dandruff, saliva, and pollen. Particularly, floating micron or sub-micron sized secretions from house dust mites, mould, pet, cockroaches, and bacteria, when inhaled, induce an immune response, resulting in the onset of inflammatory respiratory diseases.

Various kinds of bacteria and mould are found in indoor air and these inhabit the skin, the gastrointestinal tract and respiratory tract of many different organisms such as humans, pets, house dust mites and cockroaches and live or are introduced from inside or around buildings and structures.

Examples of the bacteria that are found in indoor air include *Bacillus* sp., *Staphylococcus aureus*, *Staphylococcus epidermidis*, *Staphylococcus hominis*, *Pseudomonas stutzeri*, *Pseudomonas luteola*, *Streptomycetes*, *Corynebacteriaceae*, and *Escherichia coli*.

These various bacterial air pollutants and their endotoxins (lipopolysaccharide, LPS) or peptidoglycans are known to induce the production of inflammatory cytokines from immune cells and lung epithelial cells.

Meanwhile, Gram-negative bacteria constitutively secrete outer membrane vesicles into the extracellular milieu. Extracellular vesicles secreted from Gram-negative bacteria are spherical with a size of 20-200 nm and consist of phospholipid bilayers. Gram-negative bacterial extracellular vesicles have LPS as well as various outer membrane proteins that can regulate inflammatory responses in host cells. Recently, the present inventors have reported that Gram-positive bacteria also secrete extracellular vesicles and that the extracellular vesicles contain proteins capable of inducing inflammation as analyzed by proteomic analysis.

Inflammatory respiratory diseases may be largely classified by the organ or tissue involved, for example, as upper respiratory tract infections, such as rhinitis and sinusitis, lower respiratory tract infections, such as asthma and bronchitis, small air way diseases such as bronchiolitis, and lung parenchymal diseases such as emphysema and pneumonia. From the view of clinical obstruction of the airway, respiratory diseases may be classified as asthma characterized by reversible obstruction and chronic obstructive pulmonary disease (COPD) characterized by irreversible obstruction. Chronic obstructive pulmonary disease is the co-occurrence of chronic obstructive bronchitis or chronic obstructive bronchiolitis and emphysema. A lot about allergic asthma is associated with sensitivity to indoor proteins (allergens), and so a lot of attention has focused on the increased exposure to these allergens as being the primary cause of the rise in asthma cases. Irritants such as those from smoking are associated with a greater risk of chronic obstructive pulmonary disease.

The importance of inflammation in the onset of asthma and chronic obstructive pulmonary disease have been previously reported, but inflammation patterns differ therebetween. Eosinophilic inflammation is a pathogenic correlate of asthma while non-eosinophilic or neutrophilic inflammation is responsible for chronic obstructive pulmonary disease. Rather, neutrophils accumulate in the airways in patients with asthma who have more severe airflow obstruction, where an excess of eosinophils may also be present. In addition, neutrophils are prominent in airway secretions during acute asthma, especially irreversible asthma exacerbations. Further, the etiology of chronic inflammation in the lung may be accounted for by the immune dysfunction generated in the trachea and the lung paranchyma. The present inventors previously reported that eosinophilic inflammation is associated with Th2 immune responses while neutrophilic inflammation is associated with Th1 and Th17 immune responses. It has long been suggested that inflammation may develop into cancer. Recent reports showed that Th17-mediated immune responses to a toxin derived from gut flora are associated with the onset of colorectal cancer. *Helicobacter pylori*, playing an important role in the natural stomach ecology, is known to cause not only chronic gastritis but also stomach cancer. It has been postulated that the same factor may be responsible for the etiology of both chronic obstructive pulmonary disease and lung cancer, which is supported by recent clinical studies that have showed that chronic obstructive pulmonary disease itself is an important risk factor for lung cancer, irrespective of smoking.

DISCLOSURE

Technical Problem

Leading to the present invention, intensive and thorough research into the etiology of respiratory diseases, conducted by the present inventors, resulted in the finding that extracellular vesicles derived from various microbes and organisms exist in indoor air and when inhaled into mammals, cause inflammatory respiratory diseases.

It is an object of the present invention to provide a composition comprising extracellular vesicles found in indoor air, as well as a method for the diagnosis, prophylaxis and/or therapy of inflammatory respiratory diseases, using the extracellular vesicles.

In detail, the present invention addresses an animal model of respiratory disease established by administering to the animal the extracellular vesicles present in indoor air, and a method for screening drug candidates preventive or therapeutic of a respiratory disease using the animal model. Also, the present invention provides a vaccine for the prophylaxis or therapy of respiratory diseases, a method for diagnosing pathogenic factors of a respiratory disease, a method for preventing the generation and exacerbation of respiratory diseases by inhibiting the activity of extracellular vesicles or removing extracellular vesicles from indoor air, and a method for determining indoor air quality associated with the pathology of respiratory diseases by measuring the concentration of extracellular vesicles in indoor air.

The objects of the present invention are not limited to those mentioned above, and other objects, advantages and features of the present invention should be clearly understandable by those skilled in the art from the following description.

Technical Solution

In accordance with an aspect thereof, the present invention provides a composition comprising extracellular vesicles derived from indoor air.

According to one embodiment of this aspect, the extracellular vesicles may be derived from, but are not limited to, indoor dust, house dust mites, mould, cockroaches, pet secretions, pollen, human dandruff, etc.

According to another embodiment of this aspect, the extracellular vesicles may be derived from bacteria found in indoor air which may live on (but are not limited to) indoor dust, house dust mites, mold, cockroaches, pet secretions, plants, or human dandruff.

In another embodiment, the extracellular vesicles may be in the form of a combination originating from two or more different kinds of bacteria.

In another embodiment, the bacteria belong to a genera selected from the group consisting of *Staphylococcus, Micrococcus, Enterococcus, Pseudomonas, Streptomycetes, Corinebacterium* and a mixture thereof.

In another embodiment, the bacteria is selected from the group consisting of *Staphylococcus aureus, Staphylococcus hominis, Micrococcus lylae, Enterococcus faecalis, Pseudomonas stutzeri, Pseudomonas luteola, Escherichia coli* and a mixture thereof.

In another embodiment, the extracellular vesicles may include secretions from a mould present in indoor air. The fungal extracellular vesicles are those secreted from the molds that inhabit indoor dust.

In another embodiment, the extracellular vesicles are a spontaneous secretion produced by bacteria or mold in a culture medium, or an artificial secretion produced by bacteria or mold in a culture medium.

Contemplated in accordance with another aspect of the present invention is an animal model of disease established by administering extracellular vesicles derived from indoor air to an animal.

The extracellular vesicles are as described above.

In one embodiment of this aspect, the animal model may include a mouse, but is not limited thereto.

The disease may include rhinitis, sinusitis, nasopharyngeal cancer, asthma, bronchitis, chronic obstructive pulmonary disease, bronchiolitis, pneumonia, and lung cancer.

The administration includes intranasal administration, oral administration and intratracheal administration.

In accordance with a further aspect thereof, the present invention addresses a method for screening drug candidates preventive or therapeutic of a disease, using extracellular vesicles derived from indoor air.

In this regard, the extracellular vesicles are like those described above.

The disease may be caused or exacerbated by extracellular vesicles existing in indoor air and may include rhinitis, sinusitis, nasopharyngeal cancer, bronchitis, asthma, chronic obstructive pulmonary disease, bronchiolitis, pneumonia, and lung cancer.

According to one embodiment, the method is characterized by the administration of a drug candidate to the animal model of disease of the present invention.

In another embodiment, the screening method comprises treating cells in vitro with a drug candidate in the presence of the indoor air-derived extracellular vesicles. In this context, the cells may include inflammatory cells, epithelial cells and fibroblast cells.

In another embodiment, the screening method comprises administering a drug candidate together with the extracellular vesicles derived from indoor air, and determining the level of an inflammatory mediator, but the present invention is not limited to this.

In accordance with still a further aspect thereof, the present invention provides a vaccine for the prophylaxis and therapy of a disease, comprising extracellular vesicles derived from indoor air.

The extracellular vesicles are as described above.

In this aspect, the disease may be caused or exacerbated by extracellular vesicles in indoor air and may include rhinitis, sinusitis, nasopharyngeal cancer, asthma, chronic obstructive pulmonary disease, bronchitis, bronchiectasis, bronchiolitis, pneumonia, and lung cancer.

According to one embodiment of this aspect, the disease may include sinusitis, bronchiectasis, and pneumonia which are all caused by bacteria or mould in indoor air.

In another embodiment, the extracellular vesicles may be those derived from transformed bacteria or mold so as to enhance medicinal efficacy or alleviate side effects, but the present invention is not limited to this.

In another embodiment, the extracellular vesicles may be those derived from chemically treated bacteria or mould so as to enhance medicinal efficacy or alleviate side effects, but the present invention is not limited to this.

In another embodiment, the extracellular vesicles may be chemically treated so as to have their medicinal efficacy enhanced or alleviate side effects, but the present invention is not limited to this.

In another embodiment, the extracellular vesicles may be used in combination with a drug so as to enhance the medicinal efficacy or alleviate side effects, but the present invention is not limited to this.

Also contemplated in accordance with still another aspect of the present invention is a vaccine preventive or therapeutic of infections, comprising extracellular vesicles derived from indoor air.

The extracellular vesicles are as described above.

The infection may include those caused by bacteria or mould present in indoor air. For example, the bacteria or mould are present in hospital indoor air.

According to one embodiment, the infection may include sinusitis, bronchitis, bronchiectasis, pneumonia, and sepsis, all being caused by bacteria or mould.

According to another embodiment, the extracellular vesicles may be derived from transformed bacteria or mould to enhance their efficacy or reduce their side effects, but the present invention is not limited by this.

In another embodiment, the extracellular vesicles may be derived from bacteria or mould treated with a chemical compound to enhance their efficacy or reduce their side effects, but the present invention is not limited by this.

In another embodiment, the extracellular vesicles may be treated with a chemical compound to enhance their efficacy or reduce their side effects, but the present invention is not limited by this.

In another embodiment, the extracellular vesicles may be intended to be administered in combination with a drug so as to enhance their efficacy or reduce their side effects, but the present invention is not limited by this.

In accordance with yet a further aspect thereof, the present invention provides a method for diagnosing a pathogenic factor associated with the onset or exacerbation of a disease caused by extracellular vesicles, using extracellular vesicles derived from indoor air.

In accordance with yet another aspect thereof, the present invention provides a method for diagnosing a pathogenic factor associated with the onset or exacerbation of an infection caused by bacteria or fungi, using extracellular vesicles derived from indoor air.

The extracellular vesicles are as described above.

In this regard, the disease is caused by the extracellular vesicles present in indoor air and may comprise rhinitis, sinusitis, nasopharyngeal cancer, asthma, chronic obstructive pulmonary disease, bronchitis, bronchiectasis, bronchiolitis, pneumonia, and lung cancer.

In one embodiment, the disease is caused by bacteria or mould present in indoor air and may comprise sinusitis, bronchiolitis, and pneumonia.

The infection caused by bacteria or mould includes sinusitis, asthma, chronic obstructive pulmonary disease, bronchiolitis, pneumonia, and sepsis.

In one embodiment, the diagnosis method may comprise analyzing a base sequence of a genetic material contained in the extracellular vesicles in indoor air, but the present invention is not limited by this. The genetic material may include, but is not limited to 16S rRNA.

According to another embodiment, the diagnosis method may comprise quantitatively analyzing a protein contained in extracellular vesicles in indoor air, but the present invention is not limited by this.

According to another embodiment, the diagnosis method may comprise quantitatively analyzing immune responses to extracellular vesicles present in indoor air, but the present invention is not limited by this. The immune response may be attributed to the production of an antibody that acts against extracellular vesicles present in indoor air, but the present invention is not limited by this.

The pathogenic factor may be obtained from indoor dust. Also, the diagnosis may be implemented using a sample taken from phlegm, ascites, snivel, urine or blood.

In accordance with yet still a further aspect thereof, the present invention provides a method for deactivating or removing extracellular vesicles present in indoor air so as to prevent the onset or exacerbation of a disease.

In this regard, the disease is caused by extracellular vesicles present in indoor air and may include rhinitis, sinusitis, nasopharyngeal cancer, asthma, chronic obstructive pulmonary disease, bronchitis, bronchiectasis, bronchiolitis, pneumonia, and lung cancer.

The deactivation of the extracellular vesicles may be carried out by treating the extracellular vesicles with heat or a chemical compound that specifically reacts with the extracellular vesicles, but the present invention is not limited by this. The chemical compound may include an inhibitor against a vesicular protein, LPS (lipopolysaccharide), and a peptidoglycan, all being present in the extracellular vesicles. The LPS inhibitor may be polymyxin B.

According to one embodiment, the method may employ an instrument designed to deactivate the extracellular vesicles. The instrument may be designed to treat the extracellular vesicles with heat or a chemical compound specific for the extracellular vesicles.

According to another embodiment, the instrument may be designed to remove the extracellular vesicles. The instrument may comprise a microfilter with a pore size of from 10 nm to 200 nm, but the present invention is not limited by this.

In accordance with yet still another aspect thereof, the present invention provides a method for determining indoor air quality in association with the onset or exacerbation of a respiratory disease, characterized in that extracellular vesicles in indoor air are quantitatively analyzed.

According to one embodiment, the quantitative analysis of the extracellular vesicles may be achieved by measuring a genetic material contained within the extracellular vesicles, and the genetic material may be 16S rRNA.

According to another embodiment, the quantitative analysis of the extracellular vesicles may be achieved by measuring the level of a protein in the extracellular vesicles.

According to another embodiment, the quantitative analysis of the extracellular vesicles may be achieved by counting the extracellular vesicles with the aid of a microscope. The microscope may be a high-resolution optical microscope or an electron microscope.

Contemplated in accordance with an additional aspect of the present invention is a method for preventing or treating a disease, comprising administering extracellular vesicles derived from indoor air to a mammal.

The extracellular vesicles may be as described above.

The disease is caused by extracellular vesicles present in indoor air and may include rhinitis, sinusitis, nasopharyngeal cancer, asthma, chronic obstructive pulmonary disease, bronchitis, bronchiectasis, bronchiolitis, pneumonia, and lung cancer.

In one embodiment, the disease is caused by bacteria or a mould present in indoor air and may include sinusitis, bronchiectasis, pneumonia, and sepsis.

The administering may be achieved by subcutaneous injection or transmucosal administration.

Advantageous Effects

Based on the finding that extracellular vesicles derived from bacteria and the like are present in indoor air and when inhaled, they (particularly Gram-negative bacteria-derived extracellular vesicles) may induce Th17 and/or Th1 immune responses in the lung to cause neutrophilic inflammation, which may result in respiratory diseases such as severe asthma and chronic obstructive pulmonary disease, the present invention utilizes extracellular vesicles derived from indoor air for the following purposes.

In the present invention, extracellular vesicles derived from indoor air are administered to animals to establish animal models of respiratory diseases. In turn, these animal models can be used to screen and discover drug candidates preventive or therapeutic of the respiratory diseases. It is very important to clarify the exact causative factors of a disease in order to develop drugs for the prevention or treatment thereof. For example, candidate drugs can be screened for pharmaceutical efficacy either during the course of the ex vivo treatment of cells with the causative factor or when administered to the animal model. In the present invention, a method for screening candidate drugs uses the extracellular vesicles of indoor air, and using the method, drugs useful for preventing or treating diseases caused by extracellular vesicles in indoor air can be effectively developed using the screening system and/or the animal model.

In addition, the present invention allows the factors that cause respiratory diseases such as severe asthma, chronic obstructive pulmonary disease, lung cancer, etc., to be accurately diagnosed. That is, their ability to provoke immune responses and the pathogenic factors of extracellular vesicles in indoor air are analyzed by means of base sequencing and protein assay, which can be thus applicable to the development of a method for diagnosing a pathogenic factor of a respiratory disease.

Understanding the exact factor that is causative of a disease is essential for the development of a vaccine against the disease. In the case of viral infections, pathogenic agents in attenuated forms, when administered in vivo, induce an immune response to the viruses and thus can be used as a vaccine. In practice, vaccines are used to effectively prevent many viral infections. On the basis of the fact that extracellular vesicles in indoor air act as a causative factor of respiratory diseases, the extracellular vesicles can be used to provoke immune responses thereto in the body and thus can be applied to the development of vaccines effective against the diseases.

Also, the fact that extracellular vesicles in indoor air act as a causative factor of respiratory diseases makes it possible to determine indoor air quality in terms of its generation and exacerbation of respiratory diseases by measuring the level of extracellular vesicles in indoor air. Further, the present invention can be applied to an air purifier so that the activity of extracellular vesicles in indoor air can be regulated or be nullified by, for example, chemical or thermal treatment when indoor air passes through the air purifier, thereby preventing the onset or exacerbation of respiratory diseases.

DESCRIPTION OF DRAWINGS

FIG. 21 is a diagram showing a protocol for isolating extracellular vesicles from house dust mites.

BEST MODE

Figure 1:
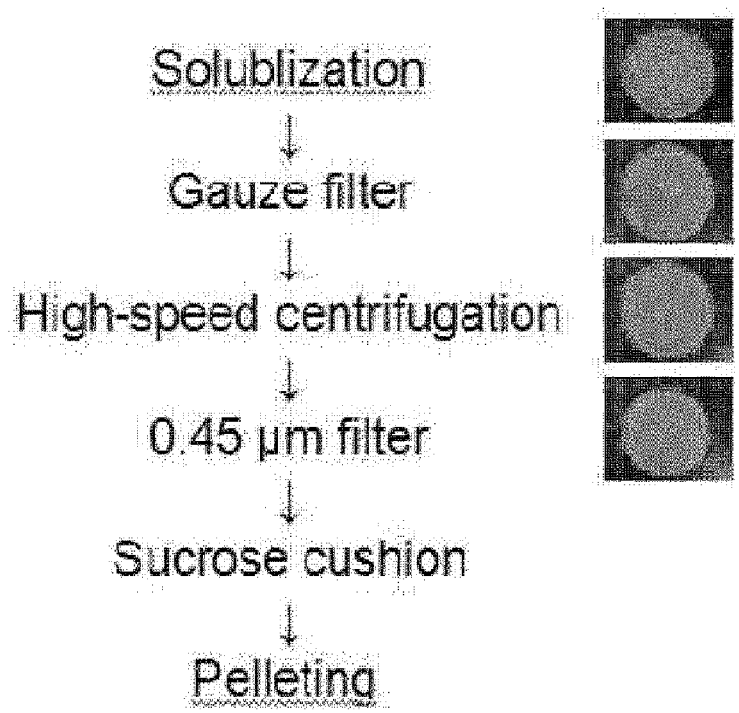
FIG. 1 shows a process of isolating extracellular vesicles from indoor dust that was collected.

The inhalation of harmful substances in indoor air may result in the onset of a respiratory disease. An allergy is a hypersensitivity disorder of the immune system. A protein alone, when inhaled, may not provoke an immune response because of immune tolerance. However, when the protein is inhaled together with an allergen, an acquired immune responses (sensitization) characterized by the memory of the protein may be induced. Given the sensitization to a protein, even a low concentration of the protein may induce an immune response, causing inflammation. Harmful gases in indoor air provoke inflammation due to their inherent toxicity, but do not induce acquired immunity. In contrast, biological contaminants in indoor may induce acquired immune responses as well as innate immune responses. However, bacterial extracellular vesicles have not been reported as existing in indoor nor have the extracellular vesicles in indoor air been disclosed as being causative factors for respiratory diseases, thus far. In the present invention, it is first reported that extracellular vesicles derived from bacteria and the like are found in indoor air and, when inhaled, can cause respiratory diseases.

Inflammation may be classified as eosinophilic inflammation and non-eosinophilic (or neutrophilic inflammation) according to the involvement of eosinophils in infiltration. Chronic inflammation occurs mainly due to abnormal immunity characterized by hypersensitivity to proteins (an acquired immune reaction). Eosinophilic inflammation takes place upon a Th2-mediated immune response to proteins whereas neutrophilic inflammation results from Th17- and/or Th1-mediated immune responses.

On the basis of the finding that the neutrophilic inflammation may be induced by the inhalation of indoor dust and is mainly due to extracellular vesicles in indoor dust and that the activity of extracellular vesicles is inhibited upon treatment with a drug (polymyxin B), an inhibitor of Gram-negative bacterial endotoxins (e.g., lipopolysaccharide (LPS)), the present inventors first disclosed that the extracellular vesicles derived from Gram-negative bacteria in indoor air are a causative factor for respiratory diseases characterized by neutrophilic inflammation.

The pathophysiology of neutrophilic lung inflammation is important in the onset of severe asthma and chronic obstructive pulmonary disease with irreversible obstruction of the airway. Chronic obstructive pulmonary disease that is characterized by neutrophilic inflammation irrespective of smoking is a risk factor for lung cancer. In practice, as many as one third of patients with chronic obstructive pulmonary disease die of lung cancer. Moreover, recent animal tests showed that Th17 immune responses and Th17-mediated neutrophilic inflammation result in lung cancer. These data indicate that Th17 immune responses and/or neutrophilic inflammation in the lung play an important role in the etiology of severe asthma and chronic obstructive pulmonary disease and are closely correlated with the generation of lung cancer.

The present invention addresses a composition comprising indoor air-derived extracellular vesicles, and the use of the extracellular vesicles in the diagnosis, prophylaxis and/or therapy of inflammatory respiratory diseases.

As used herein, the term "indoor" is intended to encompass spaces within and around buildings and structures and the term "indoor air," as used herein, is intended to encompass dust and secretions from house dust mites, cockroaches, pets, plants and humans as well as air within and around buildings and structures.

By the term "indoor air-derived extracellular vesicles," as used herein, is meant the extracellular vesicles that are present in air within and around buildings and structures. For example, indoor air-derived extracellular vesicles encompass the extracellular vesicles released from microbes that are found in indoor air or that live in the inhabitants of buildings and structures, such as house dust mites, cockroaches, pets, plants and humans. Typically, vesicles are smaller in size than their source cells, but this does not limit the scope of the present invention in any way.

Indoor air contains a variety of bacteria and mould that inhabit the skin, digestive tract and respiratory tract of various organisms including humans, pets, house dust mite, cockroaches, etc. or live within or around buildings and structures and that are introduced from the outdoor environment. A lot of dust is particularly found in bed mattresses and carpeting, providing a shelter for various bacteria and fungi. In addition, secretions from organisms such as house dust mites are found in dust. In this regard, after being isolated by removing materials of large size from the waste things that were harvested using a vacuum cleaner, dust was applied to the culture media and incubated. As a result, a number of fungal and bacterial colonies appeared. The indoor dust was solubilized in phosphate buffer saline (PBS) and subjected to multiple centrifugations to isolate extracellular vesicles. Transmission electron microscopy showed that indoor air contained spherical extracellular vesicles with a size of 50-100 nm.

An investigation was conducted to see whether indoor dust causes inflammatory respiratory disease. In this context, indoor dust was intranasally administered to C57BL/6 mice for three weeks and, 24 hours after the final intranasal administration, the total count of inflammatory cells, and particularly the neutrophil count were increased in the bronchoalveolar lavage fluid (BALF). From these results, it can be inferred that indoor dust can induce inflammatory respiratory diseases (lung inflammation) characterized by neutrophilic infiltration.

To account for the immunological mechanism of the respiratory diseases, T cell cytokines were measured using flow cytometry. The adaptive immunity of T cells is largely classified according to the cytokine secretion: a Th1 type response secretes IFN-γ; a Th2 type response secretes IL-4/IL-5/IL-13; and a Th17 type response secretes IL-17. The neutrophilic lung inflammation caused by dust is an inflammatory response mediated mainly by CD4$^+$T cells (Th17 cells) and Th1 cells that secrete IL-17 and IFN-γ, respectively. Th1 and Th17 immune responses play an important role in the pathology of inflammatory respiratory diseases (asthma, chronic obstructive pulmonary disease, bronchiolitis, pneumonia, etc.) characterized by neutrophilic inflammation in the airway and the lung parenchyma, and the onset of lung cancer. Particularly, it is known that Th1 and Th17 inflammations are correlated with the development of emphysema and lung cancer, respectively.

In relation to indoor dust-induced inflammation, an examination was made of the role of extracellular vesicles and water-soluble components of indoor dust. When extracellular vesicles and water-soluble components individually isolated from indoor dust were applied to mouse macrophages (RAW 264.7), an increased level of TNF-alpha was secreted by both of them whereas the extracellular vesicles mainly increased the secretion of IL-6. This indicates that the extracellular vesicles existing in indoor air provoke immune response and inflammation based on IL-6.

Extracellular vesicles in indoor air may be secreted from various kinds of bacteria that are present within or around buildings and structures or inhabit various organisms including humans, pets, house dust mites, cockroaches, etc. Retaining bacterial proteins, LPS and/or peptidoglycans therein, the extracellular vesicles can induce inflammatory responses.

In order to examine innate immunity to indoor air-derived extracellular vesicles in vitro, mouse macrophages (RAW 264.7) were treated with the extracellular vesicles. The macrophages were observed to secrete the inflammatory cytokines TNF-α and IL-6 in a dose-dependent manner upon treatment with extracellular vesicles.

IL (interleukin)-6 is an inflammatory cytokine that is secreted in the early stage of inflammation, serving as an index for early inflammation. IL-6 is also known to induce Th17-mediated neutrophilic inflammation. In addition, IL-6 stimulates the STAT3 signaling pathway to provoke the proliferation of pulmonary cells, angiogenesis, and the suppression of immune cells, which is related to the generation of lung cancer. Moreover, IL-6 plays an important role in differentiating naive T cells into Th17 cells upon the acquired immunity of T cells to antigens.

From the fact that extracellular vesicles in indoor air increases the secretion of IL-6 from macrophages, it can be inferred that extracellular vesicles can elicit an inflammatory response which may account for the etiology of inflammatory respiratory diseases such as asthma, chronic obstructive pulmonary disease, bronchiolitis and pneumonia as well as the onset of lung cancer.

Because extracellular vesicles in indoor air, as mentioned above, retain various proteins and LPS that can induce inflammatory responses, the roles of these inflammatory factors in the inflammatory response were evaluated.

Polymyxin B acts as an LPS inhibitor by binding to lipid A, the core component of LPS. When mouse macrophages were treated with indoor air-derived extracellular vesicles in the presence of Polymyxin B, the secretion of IL-6 and TNF-α was decreased compared to after the treatment with extracellular vesicles alone, indicating that the extracellular vesicles in indoor air comprise Gram-negative bacteria-derived extracellular vesicles.

There are a variety of proteins in the extracellular vesicles. To evaluate the functions of such vesicular proteins, the extracellular vesicles were boiled at 100° C. for 20 min before application to mouse macrophages. The thermally treated vesicles decreased the secretion of TNF (Tumor necrosis factor)-alpha, but rather increased the secretion of IL-6. This suggests that a vesicular protein induces the secretion of TNF-alpha while a heat-resistant vesicular component is responsible for the induction of IL-6 secretion.

Further, animal models of respiratory diseases can be established by administering indoor air-derived extracellular vesicles to animals. In this context, extracellular vesicles isolated from dust were administered to mice after which the generation of lung inflammation and the secretion of 11-6 were examined. The increase in inflammatory cell counts was proportional to the concentration of the extracellular vesicles administered via an intratracheal route into mice. The level of IL-6 was also increased in the mice administered with the extracellular vesicles. Accordingly, this in vivo experiment is coincident with the in vitro experiment that demonstrated the induction of IL-6 secretion by the vesicles.

An examination was made to see whether repetitive exposure to the extracellular vesicles isolated from indoor dust causes inflammatory respiratory diseases. Intratracheal administration of the vesicles for three weeks induced neutrophilic inflammation whereas this inflammation was significantly suppressed when the vesicles were administered together with Polymyxin B. This implies that the inflammation is accounted for by Gram-negative bacteria-derived extracellular vesicles.

The immunological pathology responsible for lung inflammation was examined. When vesicles isolated from dust were administered, the population of T cells expressing IFN-γ and IL-17 was significantly increased in lung tissues. Co-administration of Polymyxin B and the vesicles significantly reduced the infiltration of the cells. Taken together, these results mean that extracellular vesicles in dust induce Th1- and Th17-mediated neutrophilic lung inflammation, with the vesicular LPS playing an essential role in the induction.

Further, the production of antibodies against indoor air-derived extracellular vesicles was measured. After administration of the vesicles, significantly increased levels of IgG1 and IgG2a were detected whereas co-administration with Polymyxin B reduced the levels of vesicle-specific IgG1 and IgG2a. These results suggest that the inhalation of extracellular vesicles in indoor dust through the airway induces the production of vesicle-specific antibodies in which vesicular LPS plays an important role.

*E. coli* is a Gram-negative bacterium that inhabits the intestine. It was reported that *E. coli* exists in indoor dust and secretes extracellular vesicles. An examination was made to see whether the extracellular vesicles isolated from indoor dust comprise those derived from *E. coli*. Genetic analysis with primers for 16S rRNA characteristic of *E. coli*-derived extracellular vesicles showed the existence of *E. coli*-derived extracellular vesicles in indoor dust. In addition, extracellular vesicles in indoor dust bind to antibodies against *E. coli*-derived extracellular vesicles as measured by Western blotting. These results demonstrate the presence of *E. coli*-derived extracellular vesicles in indoor dust. *E. coli* lives mainly in the large intestine and releases extracellular vesicles. Thus, the extracellular vesicles released from *E. coli* that inhabit the intestines of house dust mite, cockroaches, pets and humans are excreted together with feces from house dust mites, etc.

After *E. coli*-derived extracellular vesicles were administered once through the airway, in vivo levels of the inflammatory mediators TNF-alpha and IL-6 were increased in a dose-dependent manner.

The effect that repetitive exposure to *E. coli*-derived extracellular vesicles has on the onset of inflammatory respiratory diseases was evaluated. Intranasal administration of *E. coli*-derived extracellular vesicles at a frequency of two per week for three weeks increased the inflammatory cell count in bronchoalveolar lavage fluid in a dose-dependent manner.

Likewise, repetitive administration of a high dose (100 ng) of the extracellular vesicles for four weeks caused emphysema. Hence, when dust containing a high concentration of pathogenic vesicles such as *E. coli*-derived extracellular vesicles is inhaled, emphysema characterized by the irreversible obstruction of the airway may follow.

Extracellular vesicles derived from indoor dust may be produced from various bacteria that live in dust or inhabit various living environments such as house dust mites, cockroaches, humans and pets.

The present inventors isolated extracellular vesicles from house dust mites. Immune responses induced by extracellular vesicles derived from house dust mites were evaluated in vitro. When treated with the extracellular vesicles, mouse macrophages secreted TNF-alpha and IL-6 in a dose-dependent manner. Further, the vesicle-induced secretion of inflammatory mediators was suppressed by Polymyxin B, an LPS inhibitor. Thus, the extracellular vesicles derived from house dust mites may cause respiratory diseases and comprise Gram-negative bacterial extracellular vesicles.

As described above, in vitro experiments showed that extracellular vesicles derived from house dust mites induce an innate immune response. This induction was evaluated in vivo. In this regard, extracellular vesicles derived from house dust mites were administered once through the airway to mice whose innate immune response was then examined. The count of the inflammatory cells that had infiltrated into the lung did increase in a dose-dependent manner, with the concomitant increase in the level of the inflammatory cytokines TNF-$\gamma$ and IL-6.

Based on the result of innate immune response in the in vivo system, extracellular vesicles derived from house dust mite were repetitively administered by inhalation and the generation of lung inflammation was examined. Administration of extracellular vesicles derived from house dust mites for three weeks induced neutrophilic lung inflammation, with a concomitant increase in the IL-17 level.

These results show that extracellular vesicles derived from house dust mites induce neutrophilic inflammation which is mediated mainly by Th17.

In the present invention, some of the bacteria that inhabit indoor dust were identified as Gram-positive bacteria, especially *Staphylococcus aureus* (*S. aureus*) and *Staphylococcus hominis*.

The first report that *S. aureus*, a Gram-positive bacterium, secretes extracellular vesicles was made by the present inventors. The induction of immune responses by *S. aureus*-derived extracellular vesicles was evaluated in vitro. For this, *S. aureus*-derived extracellular vesicles were applied to mouse macrophages. *S. aureus*-derived vesicles were observed to induce macrophages to secrete TNF-alpha and IL-6. Thus, *S. aureus*-derived extracellular vesicles may cause inflammatory respiratory diseases and lung cancer.

As described above, the in vitro experiments showed that *S. aureus*-derived extracellular vesicles induced innate immune responses. To confirm the induction in vivo, *S. aureus*-derived extracellular vesicles were administered at different doses (1 μg and 10 μg) to mice via the airway. The count of the inflammatory cells introduced into the lung of the mice increased with an increase in the concentration of the extracellular vesicles. Particularly, an excess number of neutrophils infiltrated into the lung. The bronchoalveolar fluid was also observed to contain an increased level of IL-6 in proportion to the concentration of the extracellular vesicles.

From these results, it was revealed that *S. aureus*-derived extracellular vesicles cause lung inflammation, which may lead to the expectation that the vesicles stimulate IL-6 to induce Th17-mediated adaptive immune responses.

In addition, thermally treated *S. aureus*-derived extracellular vesicles were introduced into the airway of mice in order to examine in vivo the function of vesicular proteins. Under this condition, the level of IL-6, which plays an important role in the onset of lung cancer and Th17-mediated innate immune responses, was decreased. The results showed that proteins within *S. aureus*-derived extracellular vesicles incite the production of IL-6 during the Th17-mediated lung inflammation upon the inhalation of indoor dust.

Understanding the factor that is a direct cause of a disease is essential in order to use the factor in immune regulation. The present inventors found that *E. coli*-derived extracellular vesicles in indoor air cause inflammatory respiratory diseases. Injection of a low dose of *E. coli*-derived extracellular vesicles allowed the formation of extracellular vesicle-specific antibodies and provoked T cell immune responses in which Th1 and Th17-mediated immune responses were induced so as to secrete IFN-$\gamma$ and IL-17, respectively. Vaccination with *E. coli*-derived extracellular vesicles significantly suppressed *E. coli* infection. Further, the injection of the vesicular vaccine brought about a significant reduction in the secretion of inflammatory cytokines induced by the vascular uptake of *E. coli*-derived extracellular vesicles. These results demonstrate that bacterial extracellular vesicles can be used as a vaccine for preventing diseases caused by extracellular vesicles in indoor air as well as bacterial infections.

A better understanding of the present invention may be obtained through following examples, which are set forth to illustrate, but are not to be construed as limiting the present invention.

EXAMPLES

Example 1

Isolation and Characterization of Indoor Extracellular Vesicles

Extracellular vesicles were isolated from indoor dust and characterized.

First, dust was collected from bedclothes using a vacuum cleaner. The dust caught in the filter of the vacuum cleaner was transferred to a clean vial and weighed. Five grams of the dust was solubilized at 4° C. for 12 hours in 200 mL of PBS in a beaker. Large-size substance was filtered through gauze, and the filtrate was aliquoted into high speed centrifuge tubes and centrifuged twice in succession at 4° C. and 10,000×g for 15 min. The supernatant, amounting to about 180 mL, was allowed to pass once through a membrane filter with a pore size of 0.45 μm, and the filtrate was aliquoted into 70 mL ultracentrifuge tubes, followed by ultracentrifugation at 4° C. and 100,000×g for 4 hours to afford extracellular vesicles as a pellet. The pellet was suspended in PBS.

For use in the characterization thereof, the indoor dust-derived extracellular vesicles were isolated by sucrose cushion centrifugation. In 35 mL ultracentrifuge tubes were placed 0.5 mL of 2.5 M sucrose, 1 mL of 0.8 M sucrose and 32 mL of the filtrate free of large-size substance in the order, followed by ultracentrifugation at 4° C. and 100,000×g for 4 hours. The extracellular vesicles were located between the 2.5 M sucrose layer and the 0.8 M sucrose layer at which their density matched that of the surrounding sucrose. The extracellular vesicle layer was obtained after removing the layers from the top of the tube.

Figure 2:
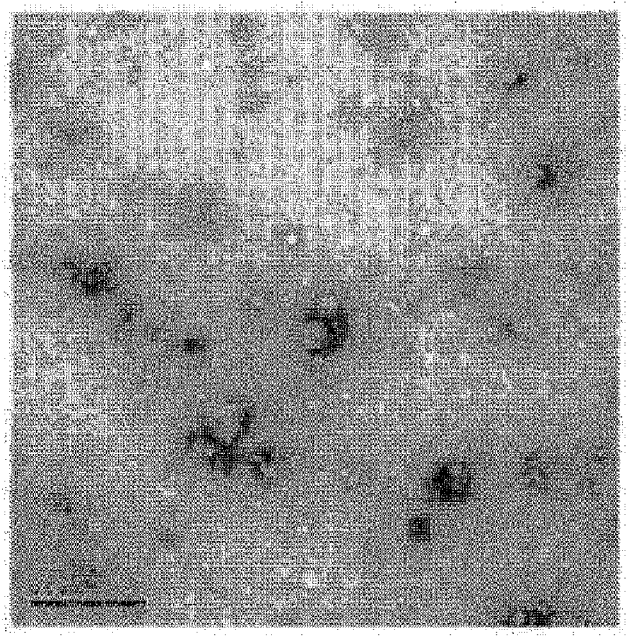
FIG. 2 shows the morphology and size of the extracellular vesicles isolated from indoor dust as analyzed by TEM (transmission electron microscope).
Figure 2:
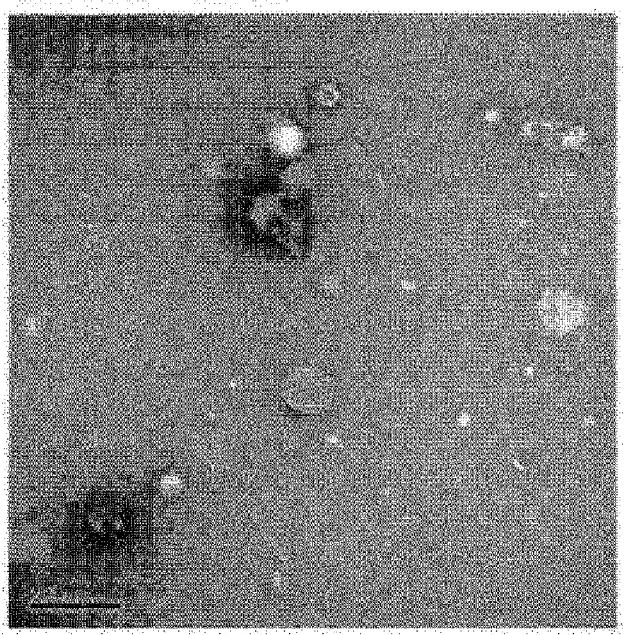

FIG. 1 is a process illustrating the isolation of extracellular vesicles from indoor dust. FIG. 2 shows indoor dust-derived extracellular vesicles that are generally spherical with a size of from 50 to 100 nm and consist of lipid bilayers as analyzed by TEM (transmission electron microscope).

From the results, it is concluded that indoor dust contains extracellular vesicles and that extracellular vesicles are present in indoor air.

Example 2

Pathogenesis of Inflammatory Respiratory Diseases (Lung Inflammation) Induced by Indoor Dust An experiment was conducted to examine whether indoor dust causes inflammatory respiratory diseases.

In this regard, 100 ng of indoor dust, whether passed through a 40 μm filter or not, was solubilized in 30 μl of PBS. The dust in PBS (phosphate buffered saline) was administered to the airway of C57BL/6 mice (6 weeks old, female), divided into groups of five on day 0, 1, 7, 8, 14 and 15, with PBS alone serving as a control. On day 16, the lung inflammation of mice was examined.

The mice were anesthetized by the intraperitoneal injection of a mixture of ketamine and xylazine. A vertical midline incision was made through which the trachea was opened so that a catheter was inserted into the airway, followed by ligation. The airway was washed twice with 1 mL of germ-free PBS. The bronchoalveolar lavage, (BAL) fluid thus obtained was centrifuged at 4° C. and 800×g for 10 min and the cell pellet was suspended in PBS. The cells were then spread over a slide by cytospin and stained with Diff Quick. Over 300 inflammatory cells were observed in a visual field magnified by 1000 times under an optical microscope and classified as basophils, lymphocytes, neutrophils, and eosinophils. Their counts were determined.

Figure 3:
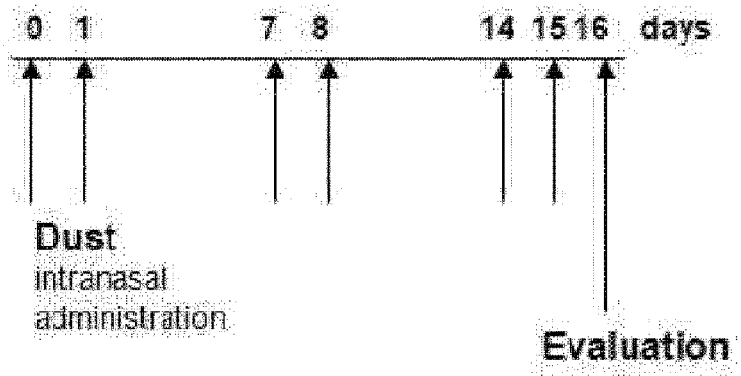
FIG. 3 is a diagram showing an experimental protocol for inducing an inflammatory respiratory disease (lung inflammation) by intranasally administering indoor dust to mice.
Figure 4:
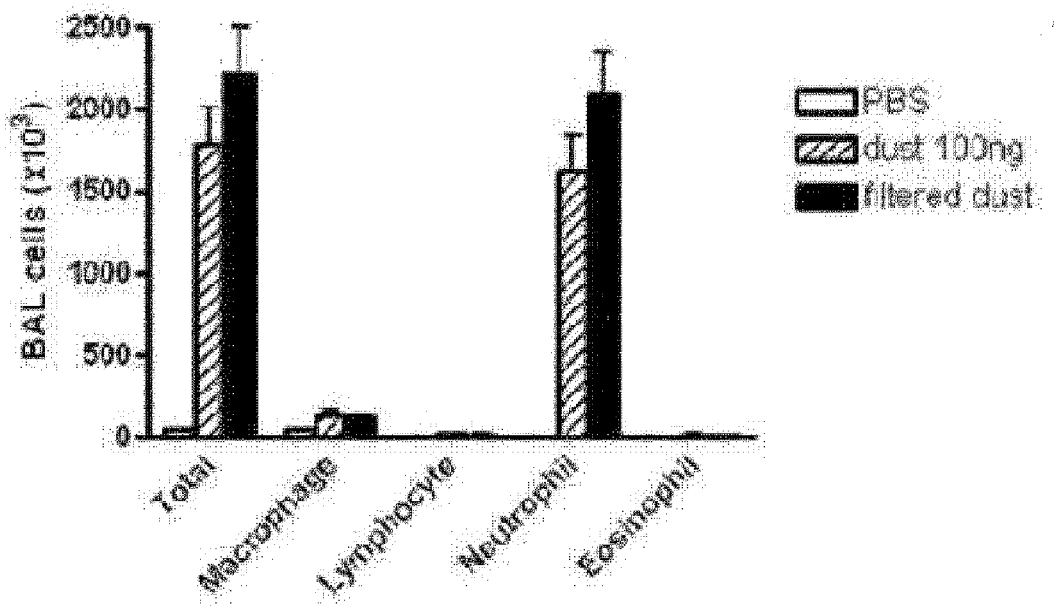
FIG. 4 is a graph showing the inflammatory cell count in bronchoalveola lavage fluid after indoor dust was intranasally administered to mice.

FIG. 3 is a diagram illustrating a protocol for inducing an inflammatory respiratory disease (lung inflammation) by intranasal injection of indoor dust. FIG. 4 is a graph showing inflammatory cell counts of BAL fluid.

As is apparent from the data of FIG. 4, the intranasal administration of indoor dust causes lung inflammation (BAL cell counts increased), with a great increase in neutrophilic infiltration. After large-size substances were removed therefrom by passage through a 40 μm filter, the dust (filtered dust), when intranasally administered, caused neutrophilic lung inflammation, indicating that of the dust components, the substance causative of neutrophilic lung inflammation is smaller in size than 40 μm.

In consequence, indoor dust, when inhaled by mammals, may cause a respiratory disease characterized by neutrophilic inflammation.

Example 3

Immunological Pathology of Neutrophilic Inflammation Induced by Indoor Dust

In relation to the pathogenicity of indoor dust for neutrophilic inflammation as revealed in Example 2, an experiment was conducted to examine the immunological mechanism.

First, a pneumonectomy was performed on the mice in which lung inflammation was induced as in Example 2. The lung thus excised was minced with a razor and incubated with collagenase type IV at 37° C. for 10 min. Then, the minced tissue was filtered through a cell strainer, followed by spinning at 4° C. and 800×g for 10 min.

The harvested cells were suspended for 10 min in a hemolysis solution to lyze red blood cells, followed by spinning again under the same conditions as above. Cells were counted using a hematocytometer and suspended at a density of $2 \times 10^6$ cells/ml in RPMI1640 supplemented with 10% FBS (fetal bovine serum) and antibiotics. The cells were seeded into 48-well plates one day before which the 48-well plates were coated with anti-CD3 and anti-CD28 antibodies by maintaining a 1 μg/ml antibody solution in PBS in an amount of 250 μl per well at 4° C. for 10~18 hours.

Then, the 48-well plates were washed with PBS to remove antibodies that did not adhere to the plate wall, but remained in free form. The pulmonary cells were placed in the plates and maintained for 4 hours. Afterwards, the cells were incubated for an additional 2 hours in the presence of 10 μg/ml brefeldin A, an antibiotic that inhibits the extracellular transport of proteins, so as to accumulate extracellular cytokines inside the cells. After incubation, the cells were stained for 30 min with fluorescence-labeled antibodies against CD4 (FITC), CD8 (PE-Cy5) and CD3 (APC). In 30 minutes, the cells were washed by centrifugation at 4° C. and 800×g for 10 min and treated with 4% formalin to form pores on the surface thereof through which antibodies against cytokines might readily enter the cells. After treatment with formalin for 10 min, the cells were stained for 30 min with fluorescence-conjugated antibodies against IFN-γ (PE), IL-4 (PE), IL-10 (PE), and IL-17 (PE). Using FACS Calibur, the expression levels of cytokines in T cells that infiltrated into pulmonary tissues were measured.

Figure 5:
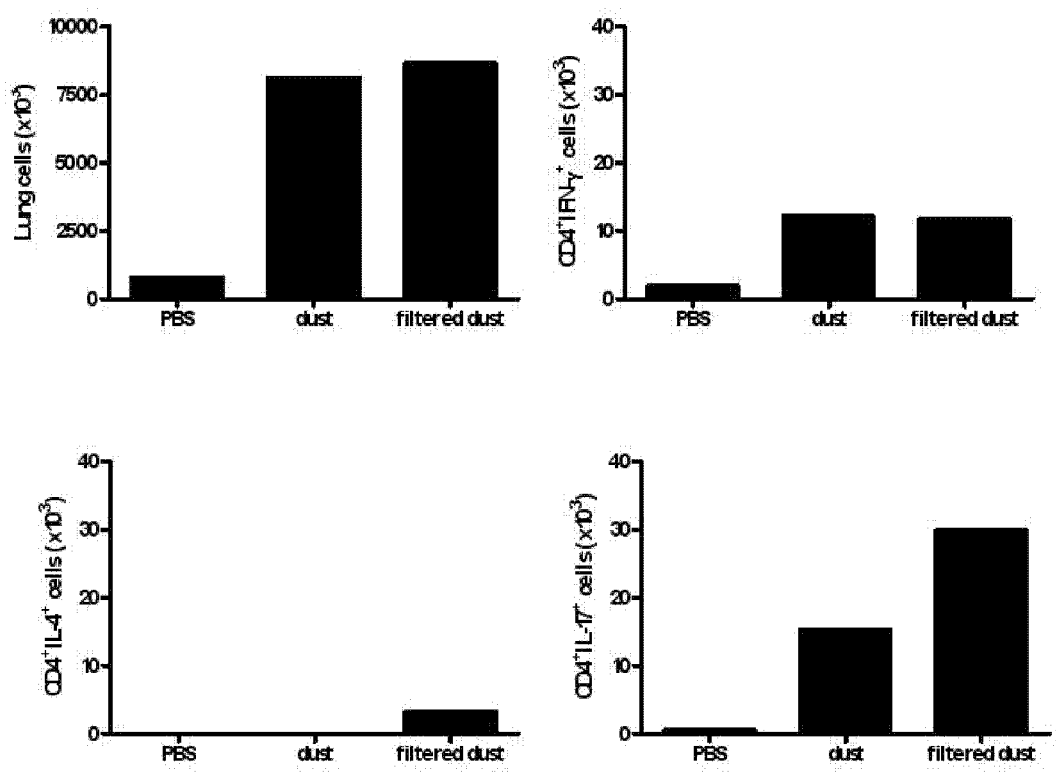
FIG. 5 shows expression levels of cytokines in CD4+ T in a pulmonary tissue, as measured by intracellular cytokine staining, after an inflammatory respiratory disease (lung inflammation) is induced by intranasally administering indoor dust to mice.

FIG. 5 shows expression levels of cytokines in CD4+ T cells as measured by flow cytometry when they are treated as described above. In FIG. 5, filtered dust is the dust after passage through a 40 μm filter as in FIG. 2. The adaptive immunity of T cells is largely classified as Th1 type response to secrete IFN-γ, Th2 type response to secrete IL-4, and Th17 type response to secrete IL-17.

As can be seen in FIG. 5, the mice in which lung inflammation was induced by dust had a higher population of CD4+ T cells secreting IFN-γ and IL-17 than did the control (PBS). The dust obtained after 40 μm filtration further increased the counts of CD4+ T cells secreting IL-17. These data demonstrate that neutrophilic lung inflammation induced by indoor dust is mediated by $CD4^+$ T cells (Th1 and Th17) secreting IFN-γ and IL-17. Th1- and Th17-mediated immune responses are immunologically hypersensitive reactions that may be involved in the pathology of inflammatory respiratory diseases on the airway and lung parenchyma, such as severe asthma, chronic obstructive pulmonary disease, bronchiolitis, pneumonia, as well as the onset of lung cancer. IFN-γ, secreted from Th1 cells, accounts for the pathology of emphysema and IL-17, secreted from Th17 cells, plays an important role in the onset of lung cancer.

From these results, it is understood that indoor dust induce Th1- and Th17-mediated immune responses which lead to the onset of inflammatory respiratory diseases characterized by neutrophilic inflammation, such as asthma, chronic obstructive pulmonary disease, bronchiolitis and pneumonia, as well as lung cancer.

Example 4

In vitro Innate Immunity Induced by Extracellular Vesicles in Indoor Air

The presence of extracellular vesicles in indoor dust, that is, indoor air was verified in Example 1. In this Example, extracellular vesicles isolated from indoor dust were evaluated in vitro for their ability to be pathogenic and provoke an innate immune response. For this, mouse macrophages (RAW 264.7) were treated with indoor dust-derived extracellular vesicles.

Indoor dust was solubilized in PBS to separate extracellular vesicles and soluble components. The induction of innate immune responses by the vesicles and the water-soluble components was examined in vitro by applying them to mouse macrophages and measuring cytokine levels in the culture media. The results are shown in FIG. 6.

In detail, mouse macrophages (RAW264.7) were seeded at a density of $1\times10^5$ cells/well into 24 well plates and maintained for 24 hours. After the cells were washed with PBS, a fresh DMEM medium was added to the cells which were then incubated for 15 hours with dust-derived extracellular vesicles (Dust-EV, 0.1 μg/ml) and soluble components (Dust-soluble, 8 μg/ml), separately. The culture media were harvested and centrifuged at 4° C. and 800×g for 10 min. Cytokines in the supernatant were quantitatively analyzed by enzyme linked immunosorbent assay (ELISA).

Figure 6:
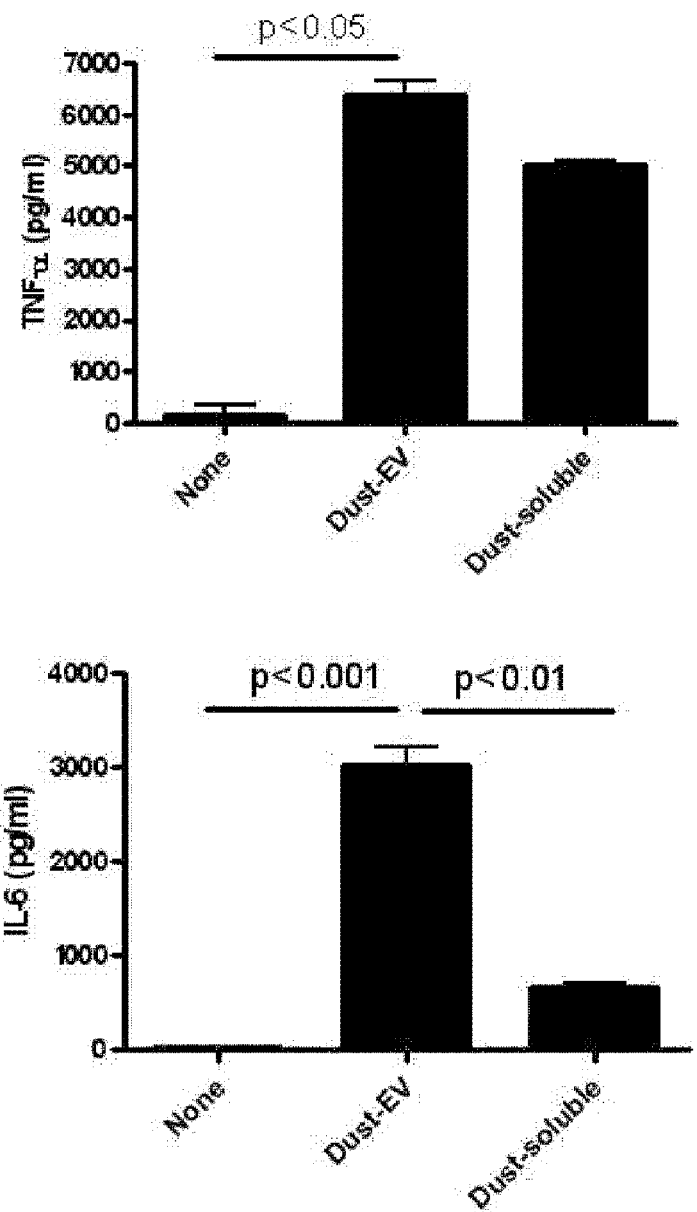
FIG. 6 shows levels of cytokines secreted by mouse macrophages, as measured by ELISA, after the mouse macrophages are treated with extracellular vesicles (Dust-EV) and water-soluble components (Dust-soluble) isolated from indoor dust.

As can be seen in FIG. 6, the secretion of INF-α was induced by both the dust-EV and the dust-soluble extracellular vesicles while IL-6 was induced mainly by the dust-EV to secrete. This indicates that the extracellular vesicles in indoor dust are mainly responsible for IL-6-mediated inflammation.

Figure 7:
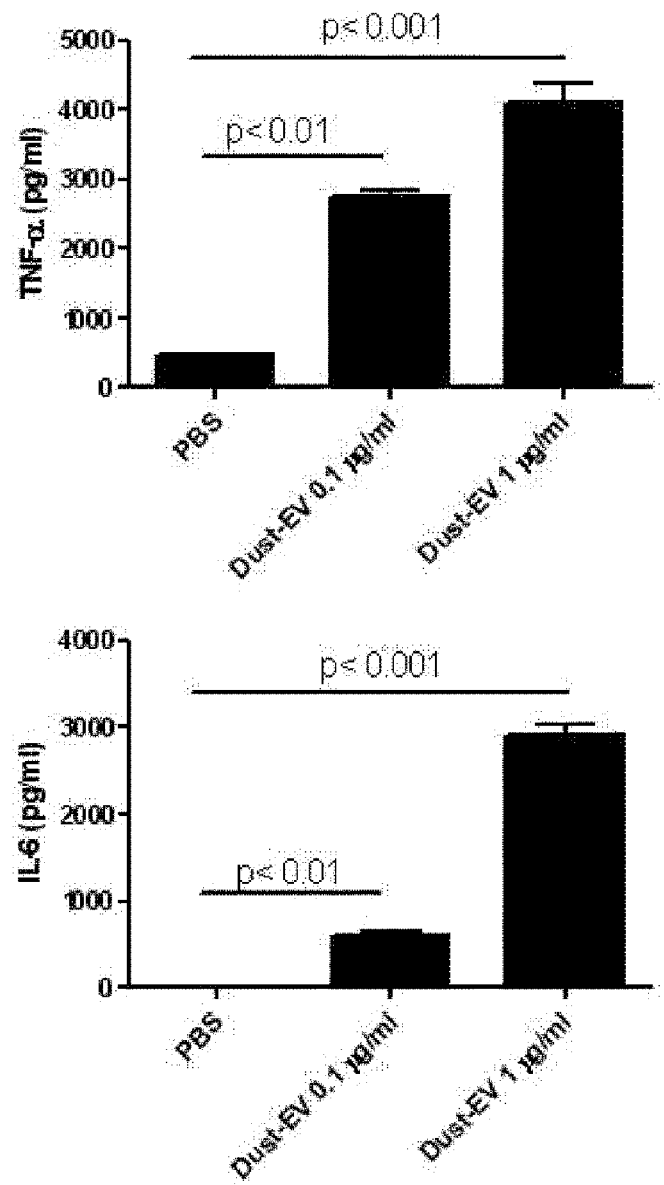
FIG. 7 shows that extracellular vesicles (Dust-EV) derived from indoor dust induce the secretion of INF-α and IL-6 cytokines from mouse macrophages in a dose-dependent manner.

In addition, cytokine levels were measured after the cells were treated with 100 ng/ml and 1 μg/ml of the extracellular vesicles in the same manner as described above. The secretion of both TNF-α and IL-6 was increased in a dose-dependent manner (FIG. 7).

Figure 8:
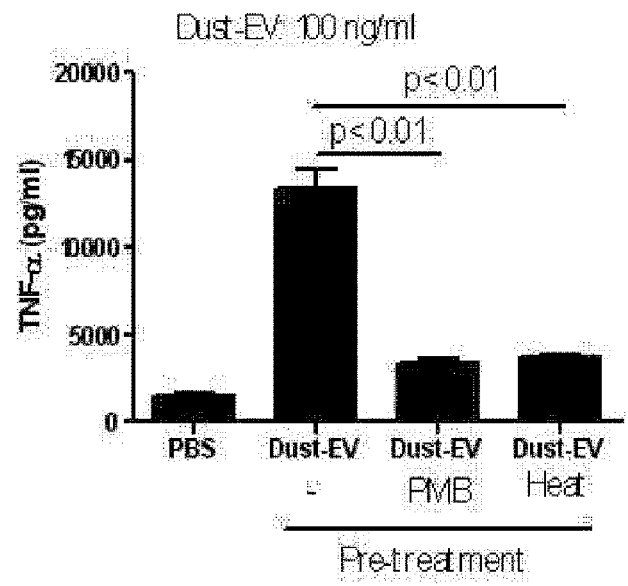
FIG. 8 shows the levels of INF-α and IL-6 secreted from mouse macrophages after the application of extracellular vesicles (Dust-EV) treated with polymyxin B (PMB) or heat to the cells.
Figure 8:
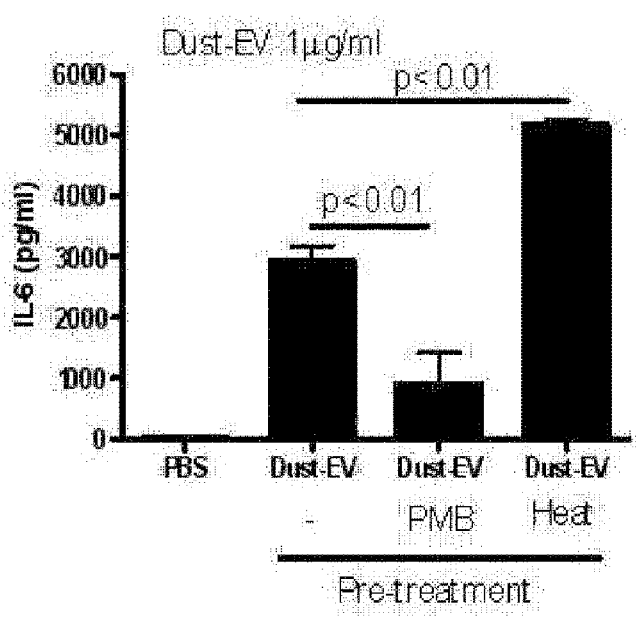

It is well known that LPS, found in the outer membrane of Gram-negative bacteria, acts as an endotoxin to induce innate immune responses and that it has been detected in indoor dust. FIG. 8 shows the roles of LPS (in the presence of the LPS inhibitor PMB (PolymyxinB)) and proteins (thermally denatured) in the immune responses induced by indoor dust-derived extracellular vesicles. The vesicle-induced secretion of TNF-α was significantly decreased upon PMB or thermal treatment. PMB also significantly reduced the vesicle-induced secretion of IL-6 whereas thermal treatment rather increased the secretion.

From the result of Example 3, it is inferred that indoor dust might induce Th17-mediated immune responses, causing neutrophilic lung inflammation. In addition, the result of Example 4 means that the neutrophilic lung inflammation upon the induction of Th17-mediated immune responses by indoor dust is closely correlated with the dust-EV-induced increase of IL-6 secretion. That is, extracellular vesicles in indoor air stimulate the secretion of IL-6, a cytokine responsible for the differentiation of T cells into Th17, thus inducing Th17-mediated immune responses and in turn causing neutrophilic lung inflammation. In addition, the pathogenicity of the vesicles to induce inflammatory respiratory disease may be accounted for by LPS.

Example 5

In vivo Innate Immune Response Induced by Extracellular Vesicles in Indoor Air

Figure 9:
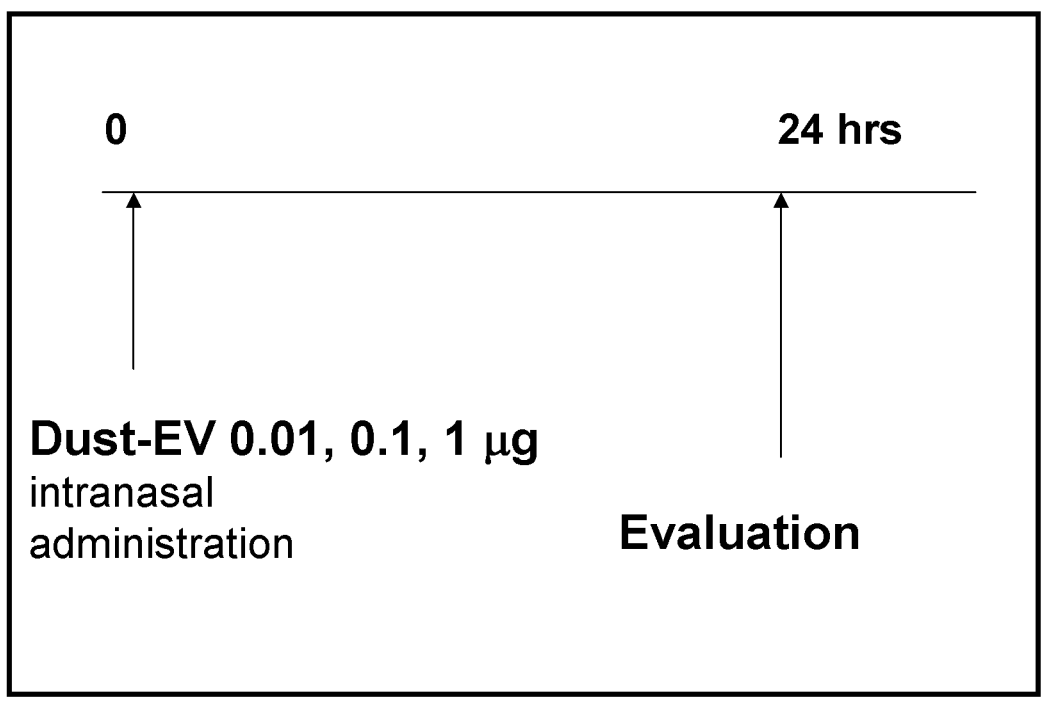
FIG. 9 is a diagram showing an experimental protocol for evaluating in vivo innate immune responses induced by extracellular vesicles present in indoor dust (Dust-EV).

In addition to the in vitro innate immune responses verified in Example 5, the in vivo innate immune response to the extracellular vesicles present in indoor air was evaluated according to the experiment protocol of FIG. 9.

C57BL/6 mice (6 weeks old, female, four in each group) were intranasally administered once with 0.01, 0.1 or 1 mg of indoor dust-derived extracellular vesicles in 30 μl of PBS. Mice injected with PBS alone were used as a control. Twenty four hours after administration, the mice were anesthetized and bronchoalveolar lavage fluid was obtained. The bronchoalveolar lavage fluid was centrifuged at 4° C. and 800×g for 10 min and the cell pellet was suspended in PBS before counting inflammatory cells introduced into the airway.

Figure 10:
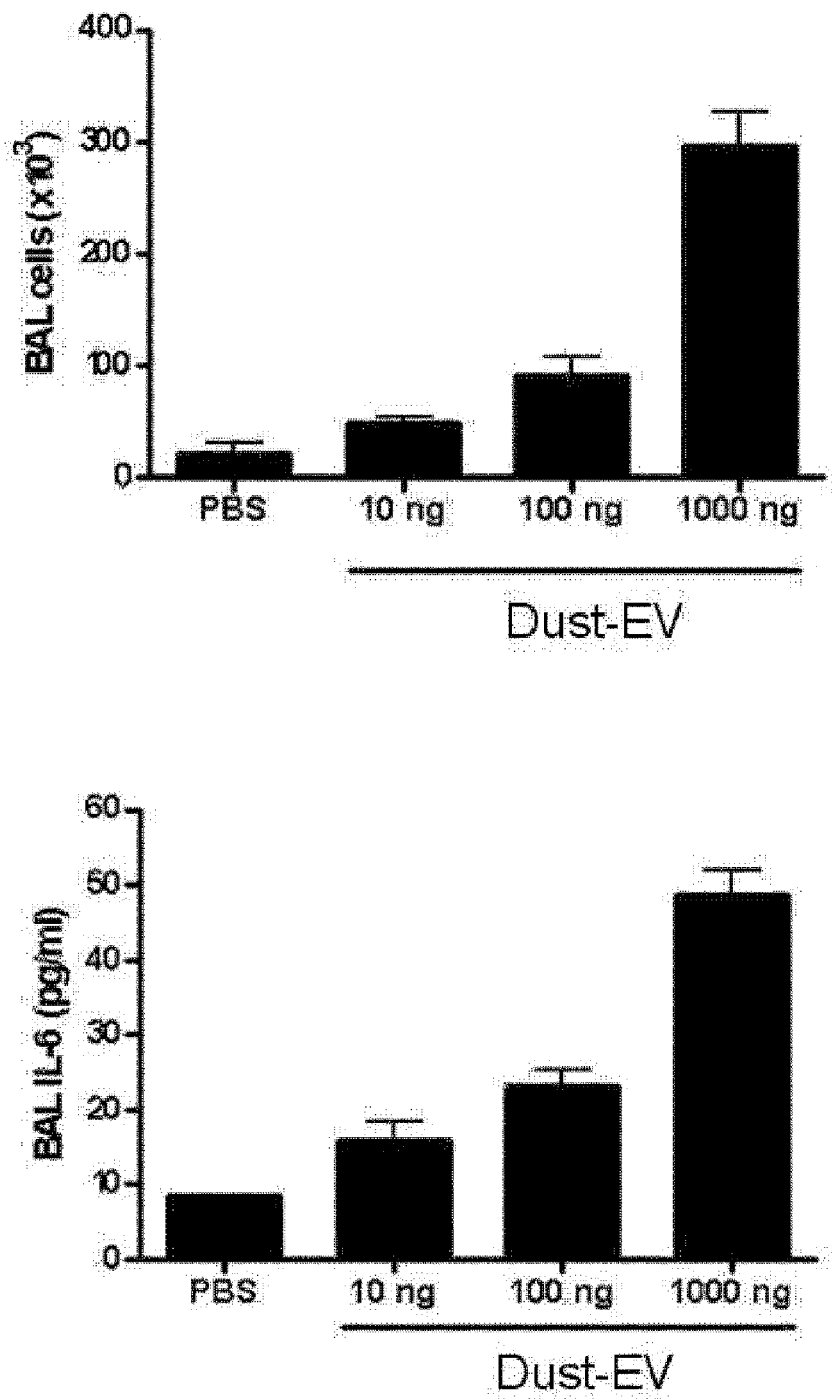
FIG. 10 shows the induction of in vivo innate immune responses upon the administration of extracellular vesicles in indoor dust (Dust-EV) according to the protocol of FIG. 9, as analyzed in the inflammatory cell count of BAL fluid.

FIG. 10 is of graphs showing the counts of inflammatory cells in bronchoalveolar lavage (BAL) fluid, which are an index for lung inflammation. As can be seen in FIG. 10, the injection of extracellular vesicles (Dust-EV) increased the inflammatory cell count of BAL fluid over the control (PBS) and in a dose-dependent manner. As for IL-6, a cytokine playing an essential role in provoking Th17-mediated immune responses, its secretion increased with an increase in the dose of the extracellular vesicles.

From these results, it is apparent that extracellular vesicles isolated from indoor dust induce innate immune responses in vitro and in vivo and promote the secretion of IL-6, thus inducing Th17-mediated immune responses and in turn causing respiratory diseases characterized by neutrophilic lung inflammation.

Example 6

Figure 11:
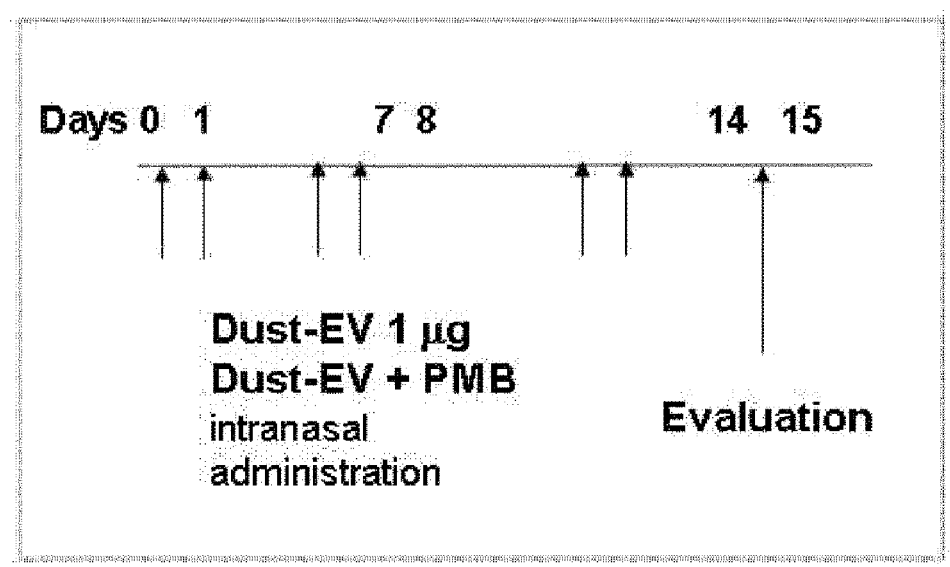
FIG. 11 is a diagram showing a protocol for evaluating the induction of in vivo acquired immune response upon the repetitive administration of indoor dust-derived extracellular vesicle (Dust-EV) and the role of extracellular vesicles and vesicular LPS in the onset of lung inflammation as a result of the immune responses.

In vivo Acquired Immune Response Induced by Extracellular Vesicles in Indoor Air According to the protocol of FIG. 11, an experiment was conducted to evaluate the induction of the in vivo acquired immune response by indoor dust-derived extracellular vesicle.

C57BL/6 mice (6 weeks old, female, four in each group) were intranasally administered twice a week for three weeks with 1 μg of indoor dust-derived extracellular vesicles in 30 μl of PBS. In addition, the vesicles were administered together with PMB so as to examine the presence and role of LPS therein. Twenty four hours after injection, clinical analysis was performed.

Figure 12:
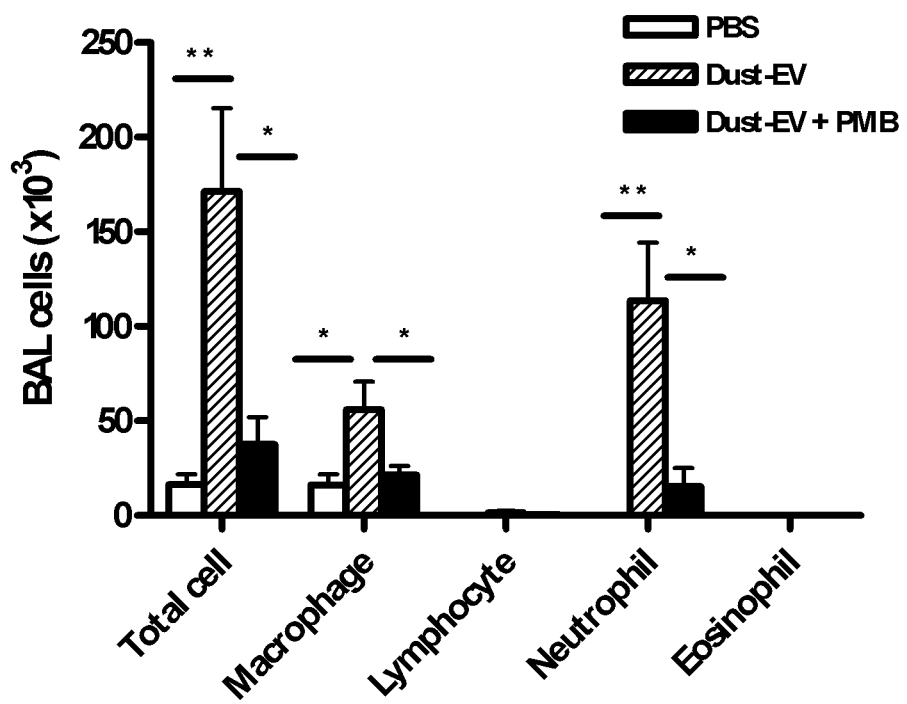
FIG. 12 is a graph showing the induction of lung inflammation upon the administration of extracellular vesicles in indoor dust (Dust-EV) according to the protocol of FIG. 11, as analyzed in the inflammatory cell count of BAL fluid.

FIG. 12 shows counts of inflammatory cells in BAL fluid, which are an index for lung inflammation. A significant increase was detected in the count of extracellular vesicle-administered group (Dust-EV), compared with that of the control (PBS). Further, the count of inflammatory cells was low after treatment with indoor dust-derived extracellular vesicles in the presence of PMB (Dust-EV+PMB), in contrast to vesicles alone. These results indicate that repetitive exposure to extracellular vesicles in indoor air causes neutrophilic inflammation, with LPS in the vesicles serving as a causative factor therefor.

Figure 13:
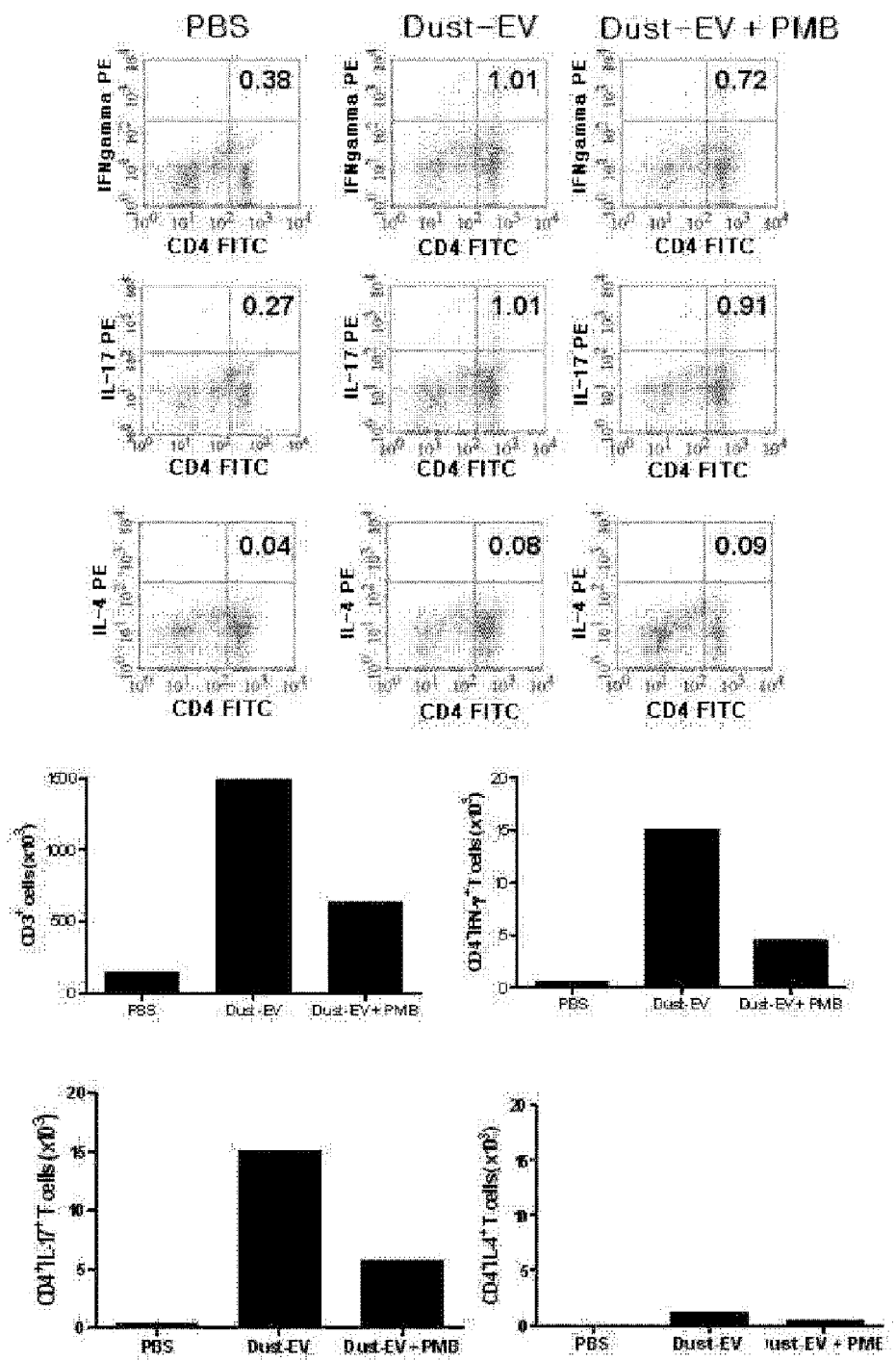
FIG. 13 shows expression patterns of IFN-γ and IL-1 in inflammatory cells isolated from local lymph nodes as measured by intracellular cytokine staining, after acquired immune responses are induced by extracellular vesicles (Dust-EV) in the presence or absence of polymyxin B (PMB) according to the protocol of FIG. 11.

Moreover, the immunological mechanism associated with the onset of lung inflammation was evaluated. Immune cells were separated from local lymph nodes and analyzed for the expression levels of IFN-γ and IL-17. The results are shown in FIG. 13. Compared to PBS, as can be seen, indoor dust-derived vesicles increased the count of T cells, particularly those secreting IFN-γ and IL-17, in local lymph nodes. In addition, the presence of PMB, in spite of treatment with extracellular vesicles, reduced the count of T cells including those secreting IFN-γ and IL-17 in local lymph nodes.

Figure 14:
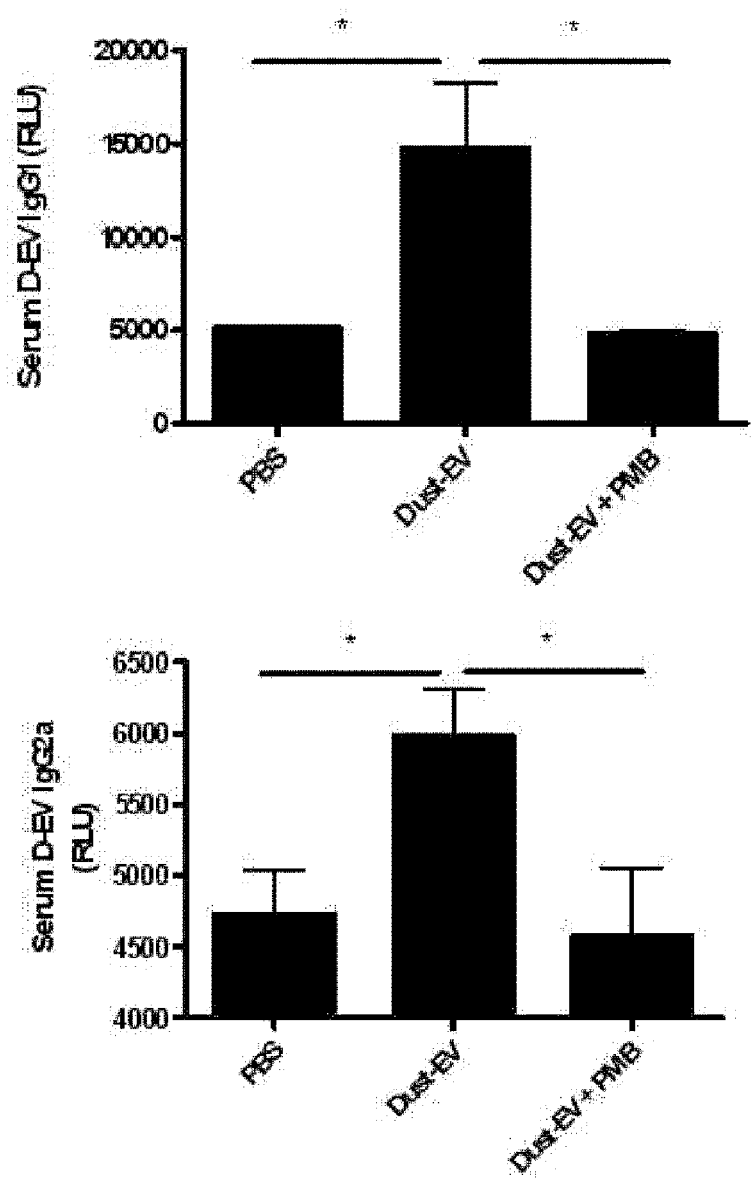
FIG. 14 shows levels of antibodies against indoor dust-derived vesicles in sera, as measured by ELISA, after treatment with extracellular vesicles (Dust-EV) in the presence or absence of polymyxin B (PMB) according to the protocol of FIG. 11.

FIG. 14 shows levels of antibodies against indoor dust-derived vesicles in sera as measured by ELISA. As is apparent from the data of FIG. 14, the levels of IgG1 and IgG2a specific for indoor dust-derived vesicles were significantly increased after injection with the vesicles, but reduced to almost the same as those of the PBS group when injected with the vesicles in combination with PMB.

From these results, it can be understood that extracellular vesicles in indoor air stimulate Th1- and Th17-mediated immune responses, resulting in lung inflammation characterized by neutrophilic inflammation, with their LPS playing an important role in the pathogenesis. Further, extracellular vesicles in indoor air, when inhaled, provoke the production of IgG1 and IgG2 antibodies specific therefor so that the analysis of vesicle-specific antibodies allows the identification of pathogenic vesicles to which the body has been repetitively exposed.

Example 7

Presence of *E. coli*-Derived Extracellular Vesicles in Indoor Air

Examples 5 and 6 showed how LPS is mainly responsible for in vivo innate and acquired immune responses induced by extracellular vesicles in indoor air. Because LPS is a lipoglycan found in the outer membrane of Gram negative bacteria, vesicles with LPS are certainly derived from Gram-negative bacteria.

Previously, the present inventors had reported that *E. coli*, a Gram-negative bacterium, is present in indoor air and releases extracellular vesicles that contain LPS as well as proteins inducing immune and inflammatory responses. Thus, a genotyping examination was made to see whether extracellular vesicles isolated from indoor dust contained *E. coli*-derived extracellular vesicles.

In this context, extracellular vesicles isolated from indoor dust were genetically analyzed using *E. coli*-specific 16s rRNA primers. The extracellular vesicles were heated at 100° C. for 20 min to elute DNA and RNA which were then used as a template for synthesizing cDNA. Two-step polymerase chain reaction (PCR) was performed on the cDNA in the presence of *E. coli*-specific 16s rRNA primers, with 40 cycles of 94° C. for 40 sec and 72° C. for 40 sec.

Figure 15:
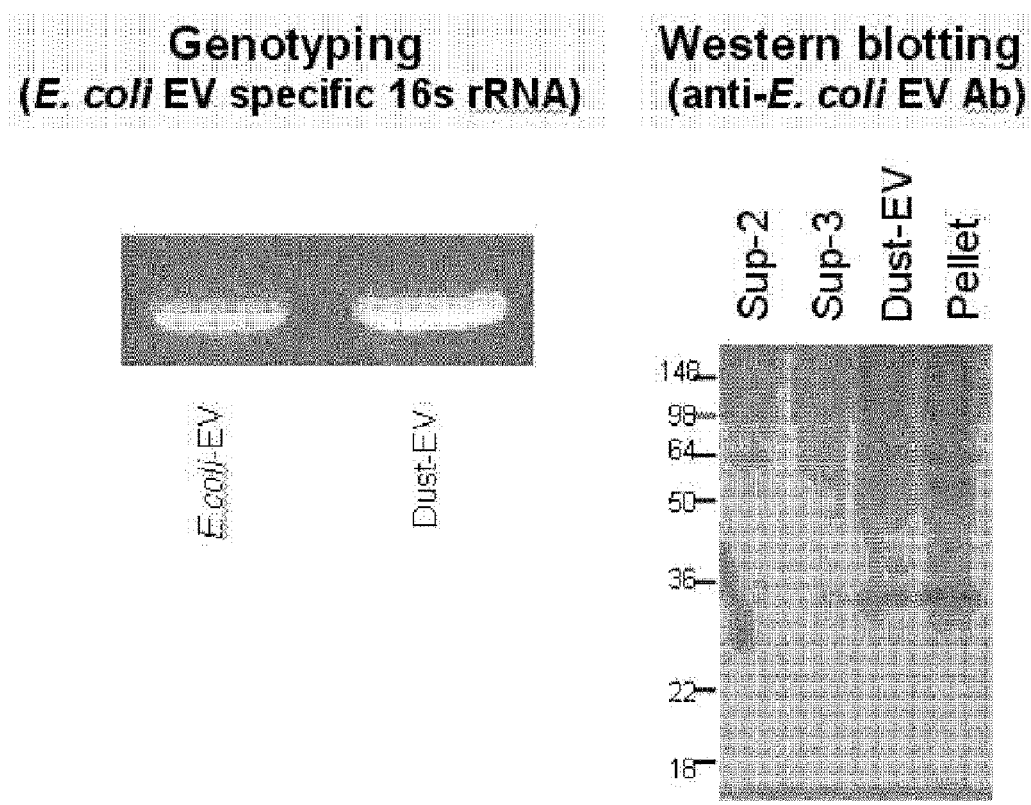
FIG. 15 shows the presence of both the E. coli 16s rRNA and a protein reactive to an antibody against E. coli-derived vesicles (E. coli-OMV) in extracellular vesicles derived from indoor dust (Dust-EV).

As a result, similar genotypes of 16s RNA were observed between *E. coli*-derived extracellular vesicles (*E. coli*-EV) and indoor dust-derived extracellular vesicles (Dust-EV) (FIG. 15).

Also, vesicular proteins were compared between *E. coli*-EV and Dust-EV. To this end, Western blotting was performed with antibodies for *E. coli*-derived extracellular vesicles (anti-*E. coli* EV Ab). As a result, proteins reacting with *E. coli*-derived vesicle-specific antibodies were detected in both a dust pellet containing bacteria and indoor dust-derived vesicles (FIG. 15).

From these results, it is apparent that extracellular vesicles derived from *E. coli* exist in indoor air.

Example 8

In vivo Innate Immune Response Induced by *E. coli*-Derived Extracellular Vesicles

*E. coli*-derived extracellular vesicles exist in indoor air as evidenced in Example 7. Based on this, the in vivo innate immune responses of *E. coli*-derived extracellular vesicles were evaluated.

*E. coli*-derived extracellular vesicles were isolated from an *E. coli* culture. *E. coli* was inoculated into 3 ml of LB broth in a test tube and cultured at 37° C. for 4 hour. From the culture, 10 μL was transferred to eight 2 L-Erlenmeyer flasks, each containing 500 ml of LB broth, and incubated at 37° C. for 4 hours. All the cultures were equally assigned to 12 350 mL-ultracentrifuge tubes and spun twice in succession at 4° C. and 5,000×g for 15 min. Nearly 4 L of the supernatant was allowed to pass once through a membrane filter with a pore size of 0.45 μm, and the filtrate was concentrated to a volume of 300 mL using the QUIXSTAND™ system with 100 kDa cutoff. After one passage of the concentrate through a membrane filter with a pore size of 0.22 μm, the resulting filtrate was ultra-centrifuged at 4° C. and 150,000×g for 3 hours in 50 mL-ultracentrifuge tubes. The pellets thus formed were re-suspended in PBS to separate extracellular vesicles derived from *E. coli*.

The immune responses induced by *E. coli*-derived extracellular vesicles were examined. C57BL/6 mice (6 weeks old, female, 4 in each group) were intranasally administered once with 1, 10, and 100 ng of *E. coli*-derived extracellular vesicles in 30 μl of PBS, 2, 8 and 24 hours after which secreted inflammatory cytokines were quantitatively analyzed. The mice were anesthetized as described above and sacrificed to obtain their BAL fluid.

Figure 16:
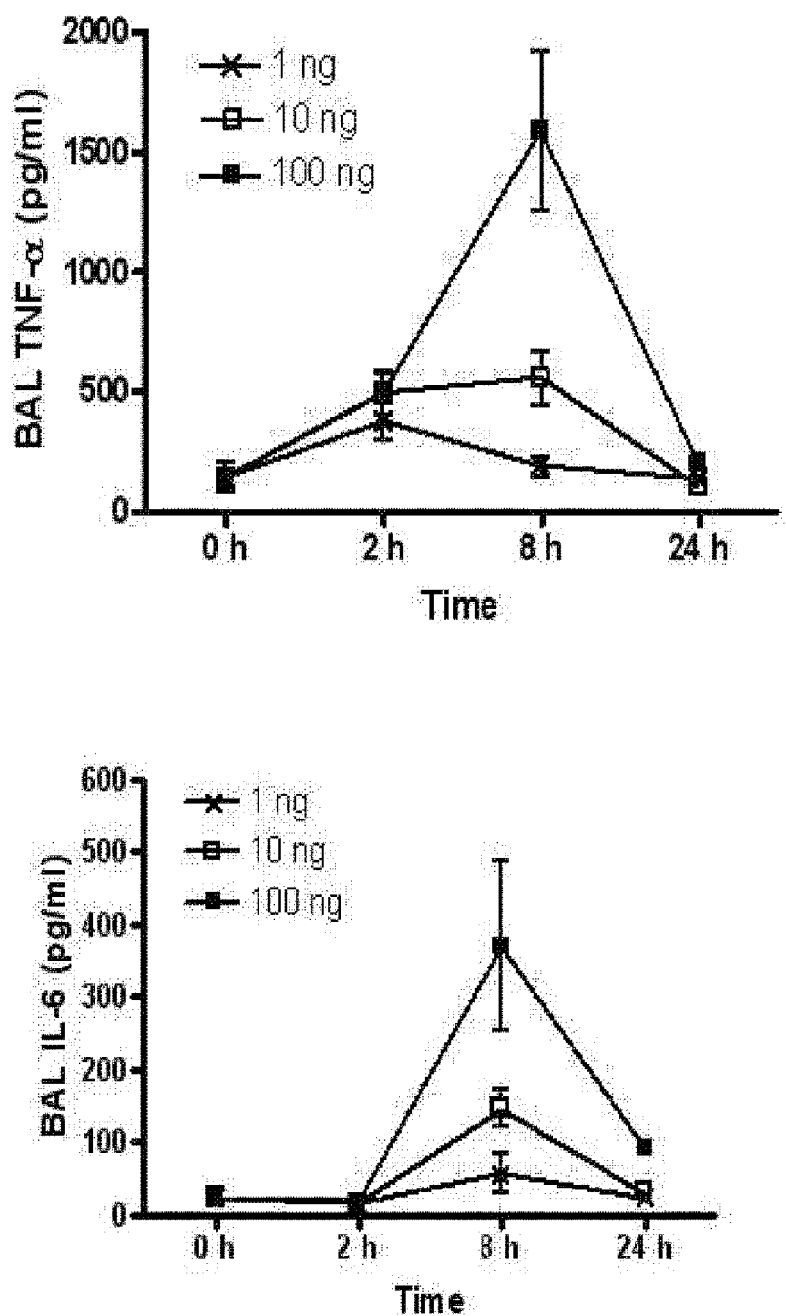
FIG. 16 shows the levels of inflammatory cytokines in BAL fluid after one intranasal injection of E. coli-derived extracellular vesicles

FIG. 16 shows the levels of inflammatory cytokines induced by *E. coli*-derived extracellular vesicles in the BAL fluid. As shown in the graphs, the levels of INF-α and IL-6 in the BAL fluid increased in a dose-dependent manner for 8 hours after administration of the vesicles.

Example 9

Induction of Lung Inflammation Induced by Repetitive Administration of *E. coli*-Derived Extracellular Vesicles Based on the fact, disclosed in Example 8, that *E. coli*-derived vesicles induce the secretion of IL-6, an inducer of Th17-mediated immune responses, in a dose-dependent manner, the vesicles were repetitively administered to induce lung inflammation.

Figure 17:
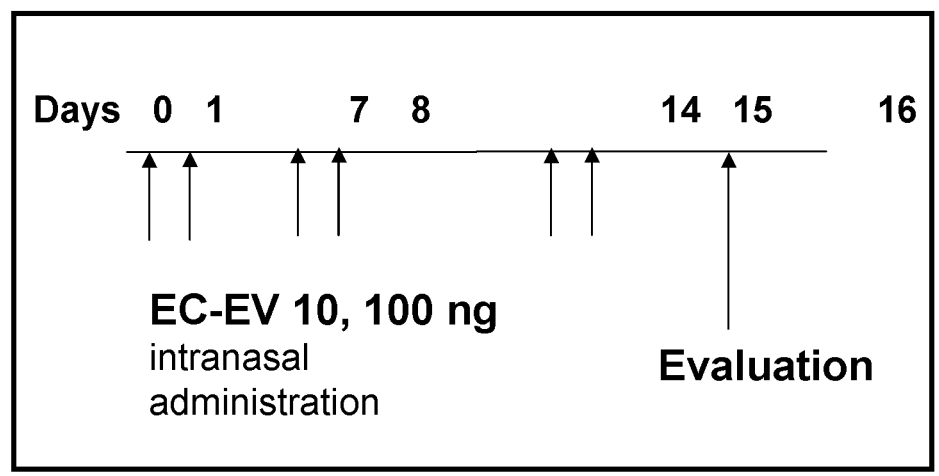
FIG. 17 is a diagram showing a protocol for evaluating lung inflammation caused upon the repetitive administration of E. coli-derived extracellular vesicles (EC-EV) over three weeks.

According to the protocol of FIG. 17, C57BL/6 mice (6 weeks old, female, 4 in each group) were intranasally administered twice a week for three weeks with 10 and 100 ng of the extracellular vesicles in 30 μl of PBS. An evaluation was made 24 hours after the final administration.

Figure 18:
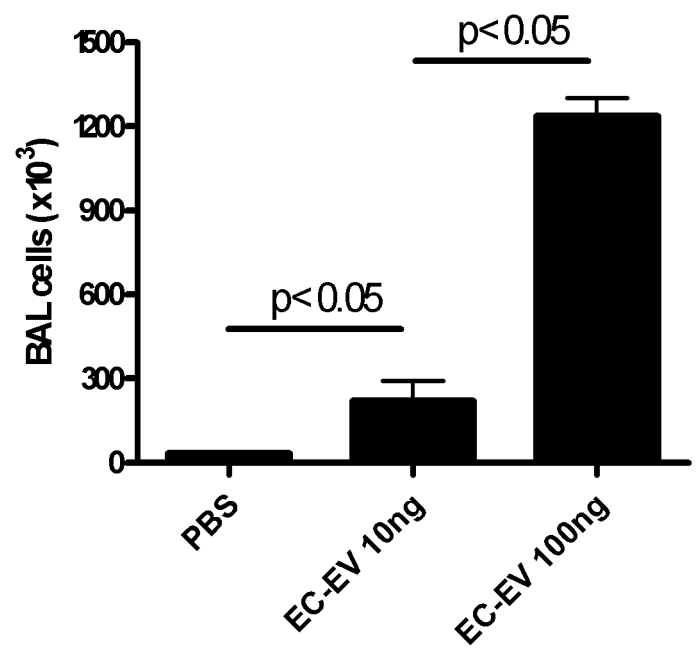
FIG. 18 is a graph showing the inflammatory cell count of BAL fluid, which is an index for lung inflammation, after E. coli-derived extracellular vesicles (EC-EV) are repetitively administered.

FIG. 18 is a graph showing counts of inflammatory cells in BAL fluid, which are the index for lung inflammation. The count of inflammatory cells was higher upon the administration of *E. coli*-derived extracellular vesicles (EC-EV), compared to the control (PBS), and increased in a dose-dependent manner.

Example 10

Emphysema Induced by *E. coli*-Derived Extracellular Vesicles

On the basis of the fact, disclosed in Example 9, that the repetitive administration of *E. coli*-derived extracellular vesicles for three weeks induces lung inflammation in a dose-dependent manner, a high dose of the vesicles was injected many times for 4 weeks so as to elicit a histological change.

Figure 19:
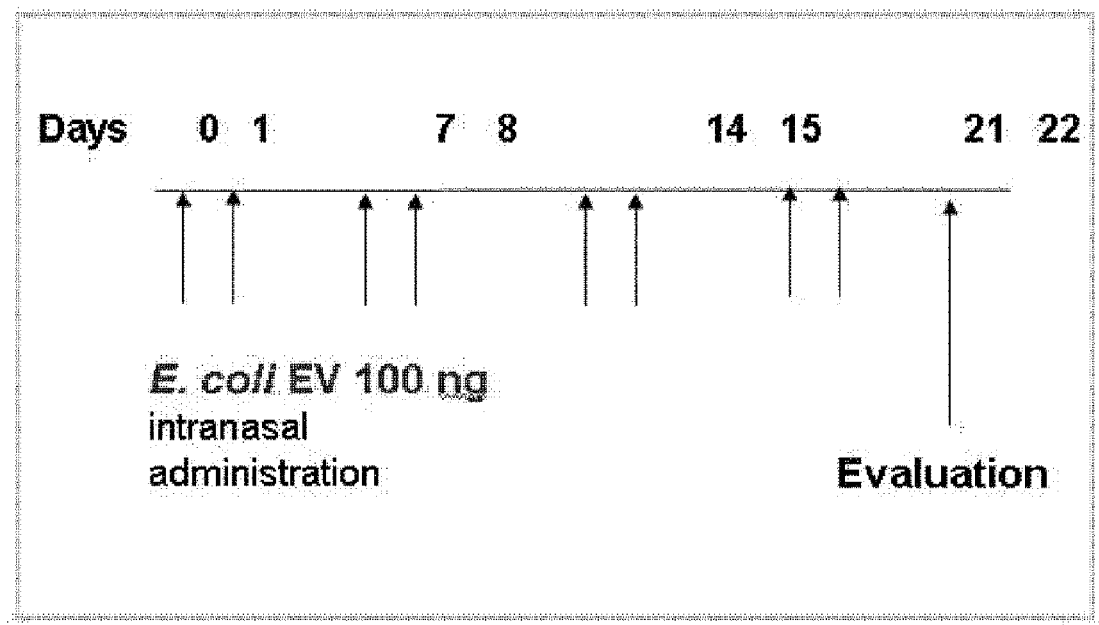
FIG. 19 is a diagram showing a protocol for evaluating histological changes upon the repetitive administration of a high dose of E. coli-derived extracellular vesicles (EC-EV) over 4 weeks.

According to the protocol of FIG. 19, 100 ng of *E. coli*-derived extracellular vesicles in 30 μl of PBS was intranasally injected twice a week for 4 weeks into C57BL/6 mice (6 weeks old, female, 4 in each group), 24 hours after which a histological change was examined.

Figure 20:
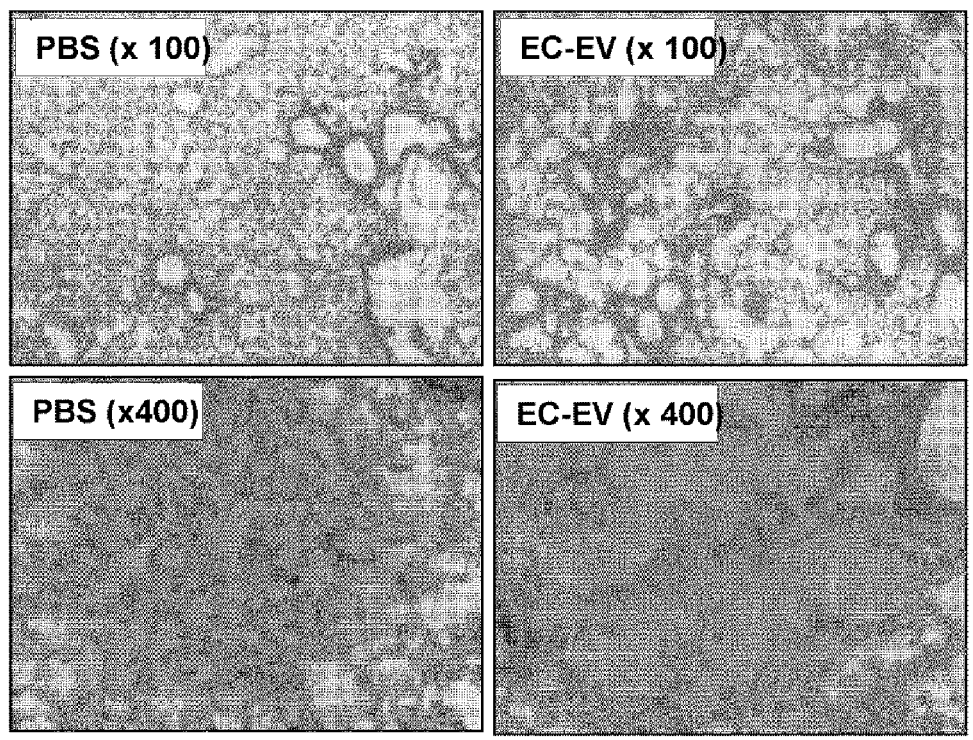
FIG. 20 shows pulmonary tissues affected by emphysema characterized by destroyed alveoli after administering E. coli-derived vesicles according to the protocol of FIG. 19

FIG. 20 shows alveolar tissues. As shown in the photographs of FIG. 20, emphysema characterized by destroyed alveoli was found in the group administered with *E. coli*-derived vesicles and the chord length was greatly increased upon the administration of the vesicles, compared to the control.

This result means that repetitive exposure to a high dose of *E. coli-extracellular* vesicles leads to the onset of emphysema characterized by irreversible obstruction of the airway.

Example 11

Preparation of Crude Extract from House Dust Mites in Indoor Air and Isolation and Characterization of Extracellular Vesicles Extracellular vesicles were isolated from house dust mites (HDM) and characterized.

To this end, 20 g of HDM, purchased from the Arthropods of Medical Importance Resource Bank, Yonsei University, was placed in 500 mL of PBS in a clean beaker and stirred at 4° C. for 24 hours. Thereafter, the PBS was assigned to high speed centrifuge tubes and centrifuged twice in succession at 4° C. and 10,000×g for 15 min. The supernatant, amounting to 450 ml, was passed once through a membrane filter with a pore size of 0.22 μm, followed by the ultracentrifugation of the filtrate in 70 ml-ultracentrifuge tubes at 4° C. and 100,000×g for 3 hours. The pellet thus formed was suspended in PBS.

For characterization, the extracellular vesicles were further purified using Opti-prep solution. A suspension of the pellet in 4.8 mL of 50% Opti-prep solution was placed in a 10 mL-ultracentrifuge tube, followed by the addition of 3 mL of a 40% Opti-prep solution and 2.5 mL of 10% Opti-prep solution to the suspension in that order. A white layer between the 40% Opti-prep solution and the 10% Opti-prep solution formed after ultracentrifugation at 4° C. and 100,000×g for 2 hours. Liquid was sequentially removed from the top in 1 mL portions, assigned to new respective tubes and mixed with 9 mL of PBS in each tube. Ultracentrifugation of the mixture in 10 mL ultracentrifuge tubes at 4° C. and 100,000×g for 2 hours afforded extracellular vesicles as a pellet. This pellet was dissolved in 1 mL of PBS.

Figure 22:
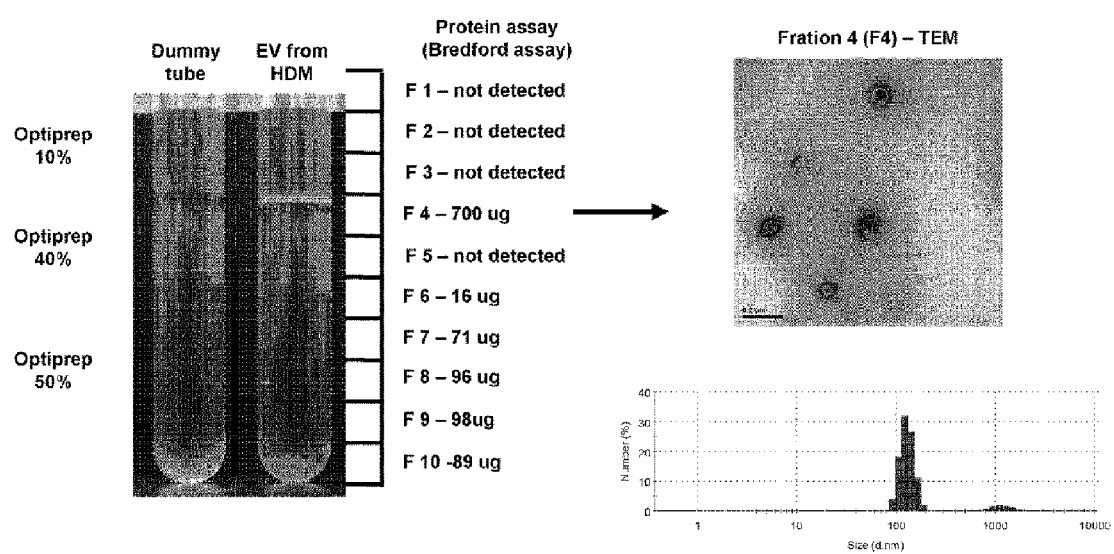
FIG. 22 shows the morphology and size of extracellular vesicles isolated from house dust mites, as analyzed by transmission electron microscope (TEM) and dynamic light scattering (DLS).

FIG. 21 shows the procedure by which extracellular vesicles were separated from house dust mites. FIG. 22 shows that extracellular vesicles of house dust mites are generally spherical with a size of 100-200 nm and consist of lipid bilayers as analyzed by TEM (transmission electron microscopy) and DLS (dynamic light scattering).

These results demonstrate that extracellular vesicles are present in an extract from house dust mites.

Example 12

In Vitro Innate Immune Response Induced by Extracellular Vesicles Derived from House Dust Mites in Indoor Air The presence of extracellular vesicles in house dust mites was verified in Example 11. In this Example, extracellular vesicles isolated from house dust mites were evaluated in vitro for pathogenicity to provoke innate immune responses. For this, mouse macrophages (RAW 264.7) were treated with extracellular vesicles derived from house dust mites.

In detail, mouse macrophages (RAW264.7) were seeded at a density of $1 \times 10^5$ cells/well into 24 well plates and grown for 24 hours. After the cells were washed with PBS, a fresh DMEM medium was added to the cells which were then incubated for 15 hours with 100 ng, 1 μg and 10 μg of house dust mite-derived extracellular vesicles (HDM-EV). The culture media were harvested and centrifuged at 4° C. and 800×g for 10 min. Cytokines in the supernatant were quantitatively analyzed by enzyme linked immunosorbent assay (ELISA).

Figure 23:
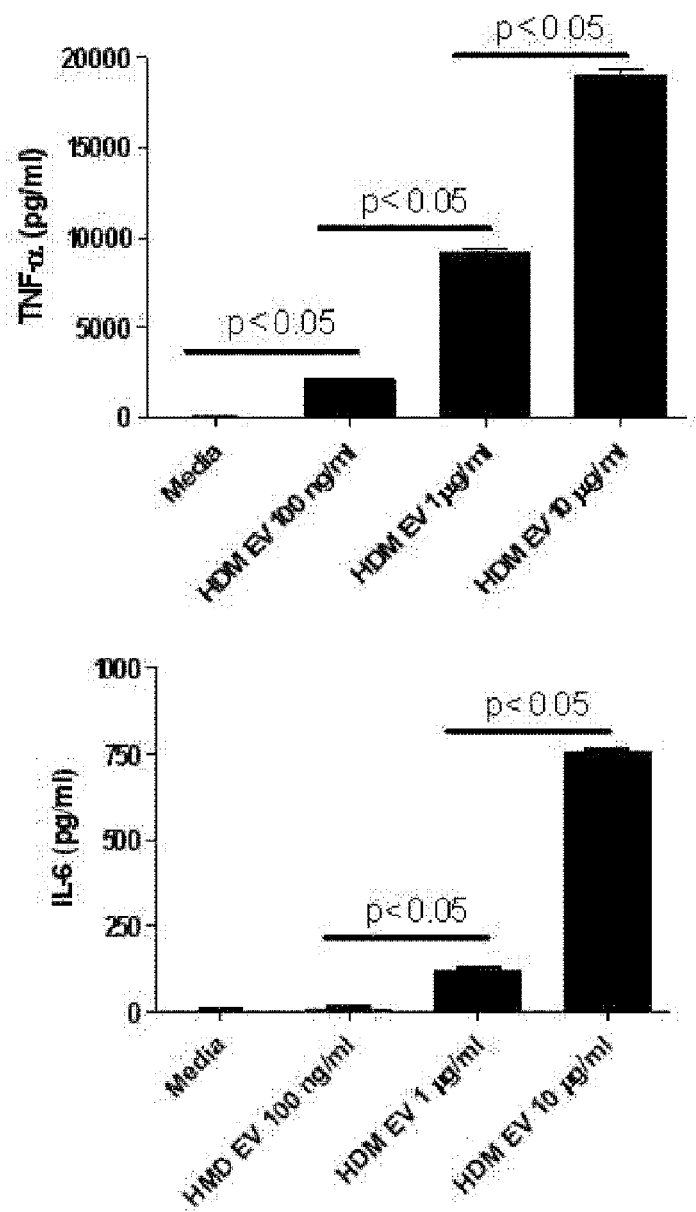
FIG. 23 shows levels of cytokines secreted in mouse macrophages after treatment with house dust mite-derived extracellular vesicles (HDM-EV).

As can be seen in FIG. 23, the secretion of INF-α and IL-6 was induced by HDM-EV and increased in a dose-dependent manner.

Example 13

In Vivo Innate Immune Response Induced by Extracellular Vesicles Derived from House Dust Mites in Indoor Air Extracellular vesicles present in house dust mites as evidenced in Example 11 were found to induce immune responses as measured in Example 12. Based on these findings, the in vivo innate immune response to HDM-EV was evaluated.

C57BL/6 mice (6 weeks old, female, five in each group) were intranasally administered once with 0.1, 1 and 10 μg of HDM-EV in 30 μl of PBS, 12 hours after which the infiltration of inflammatory cells and the secretion of inflammatory cytokines were quantitatively analyzed. Mice administered with PBS alone were used as a control. The mice were anesthetized as described above and sacrificed to obtain BAL fluid.

Figure 24:
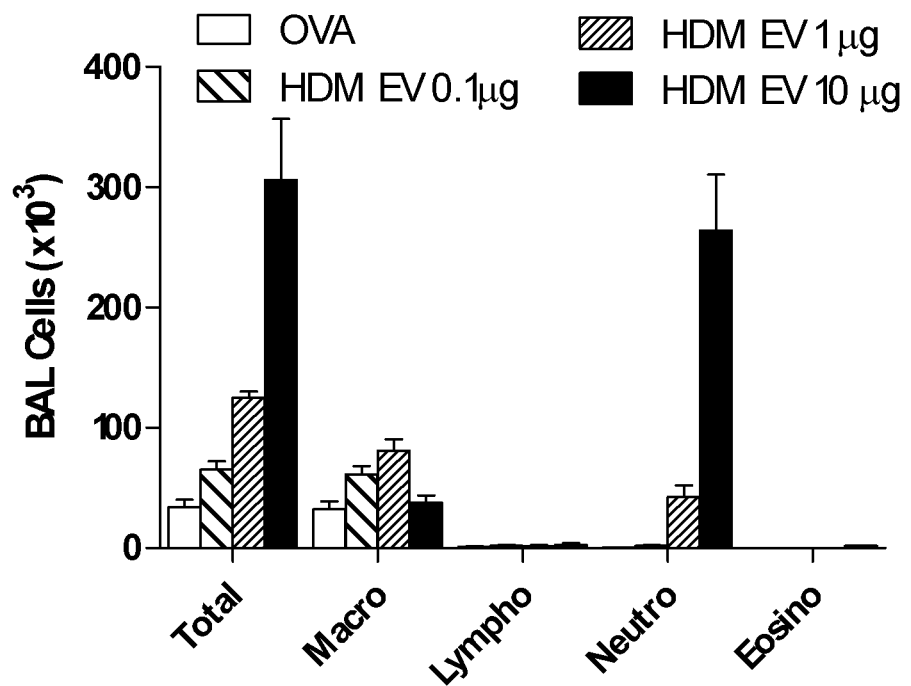
FIG. 24 is a graph showing the induction of in vivo innate immune responses upon the administration of house dust mite-derived extracellular vesicles (HDM-EV), as analyzed in the inflammatory cell count of BAL fluid.

FIG. 24 is a graph showing counts of inflammatory cells in BAL fluid, which are the index for lung inflammation. The count of inflammatory cells was higher upon the administration of HDM-EV, compared to the control (PBS), and increased in a dose-dependent manner.

Figure 25:
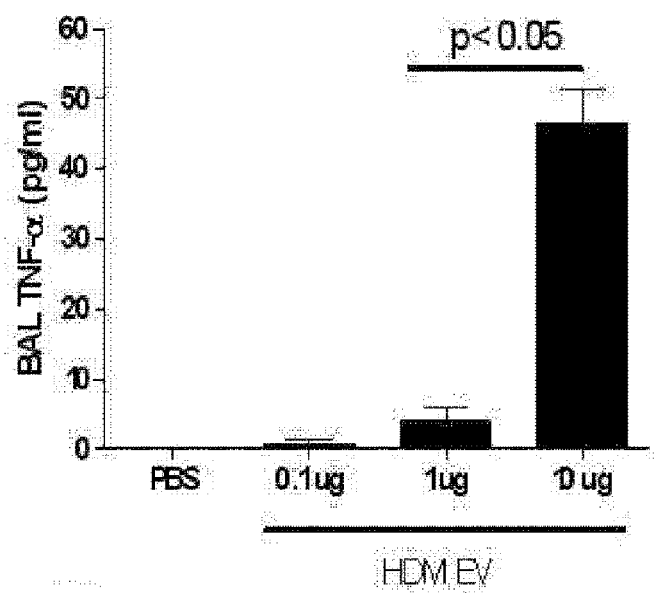
FIG. 25 shows the induction of in vivo innate immune responses upon the administration of house dust mite-derived extracellular vesicles (HDM-EV), as analyzed by the level of cytokines in BAL fluid.
Figure 25:
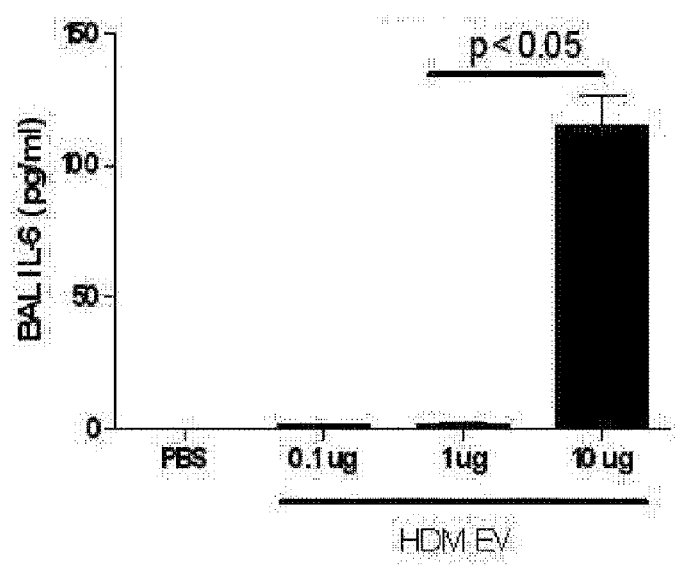

FIG. 25 shows the levels of inflammatory cytokines in BAL fluid. As shown in the graphs of FIG. 25, the administration of HDM-EV increased the levels of INF-α and IL-6 in BAL fluid in a dose-dependent manner, with a significant increase of INF-α and IL-6 at a dose of 10 μg of the vesicles.

Example 14

Induction of Lung Inflammation Induced by Repetitive Administration of Extracellular Vesicles Derived from House Dust Mites in Indoor Air HDM-EV induces immune responses as verified in Example 13. In this Example, HDM-EV was examined for its ability to provoke an acquired immune response in vivo.

C57BL/6 mice (6 weeks old, female, five in each group) were intranasally injected with 10 μg of HDM-EV once a day for three days for sensitization and then twice a week for two weeks. An evaluation was made of the infiltration of inflammatory cells and the secretion of inflammatory cytokines 24 hours after the final administration.

Figure 26:
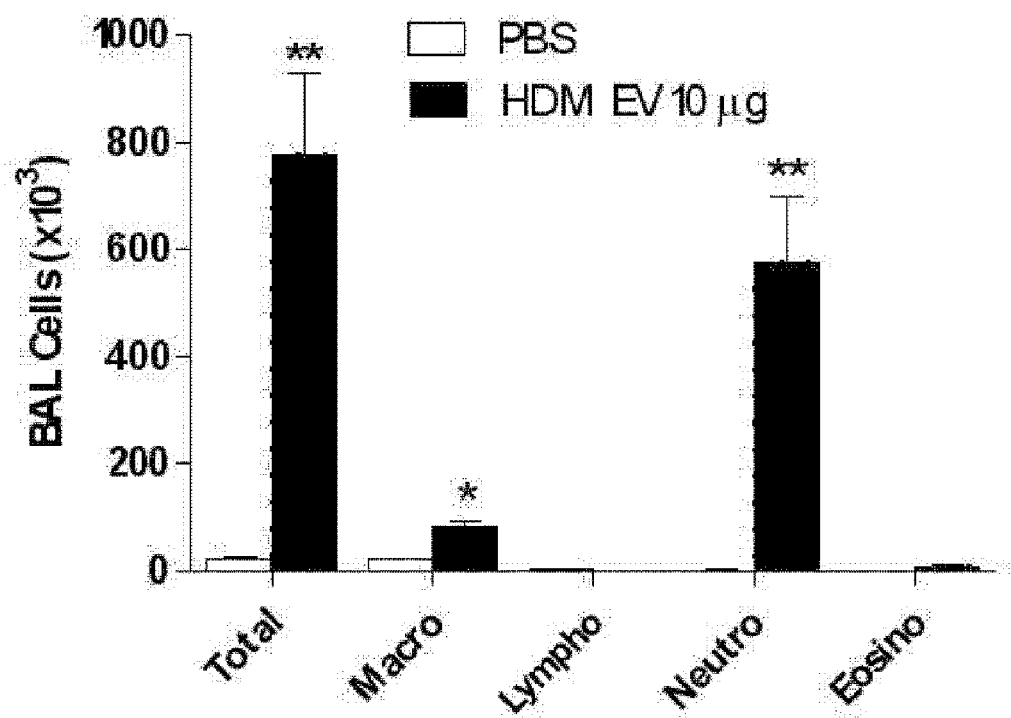
FIG. 26 is a graph showing the induction of in vivo acquired immune responses upon the administration of house dust mite-derived extracellular vesicles (HDM-EV), as analyzed in the inflammatory cell count of BAL fluid, which are an index for lung inflammation.

FIG. 26 shows the infiltration of inflammatory cells. As can be seen, a greatly increased level of inflammatory cells, especially neutrophils, was found in the bronchoalveolar lavage fluids of the group administered with HDM-EV, compared to the control group (PBS).

Figure 27:
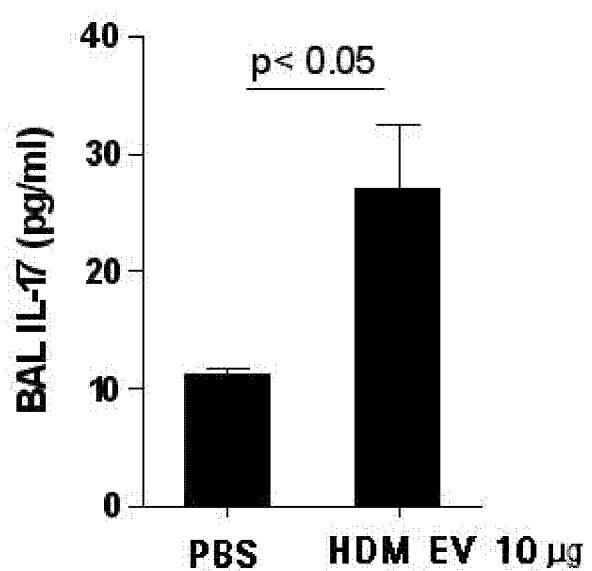
FIG. 27 is a graph showing the induction of in vivo acquired immune responses upon the administration of house dust mite-derived extracellular vesicles (HDM-EV), as analyzed by the level of IL-17, secreted from Th17, in BAL fluid.

FIG. 27 shows the expression levels of cytokines in BAL fluid, as measured by ELISA for analyzing an acquired immune response. As can be seen, the administration of HDM-EV significantly increased the levels of IL-17, secreted from Th17 cells.

These results show that the inhalation of extracellular vesicles present in house dust mites may cause neutrophilic inflammation characterized by a Th17-mediated immune response.

Example 15

Cultivation and Identification of Bacteria and Mould Present in Indoor Dust

Figure 28:
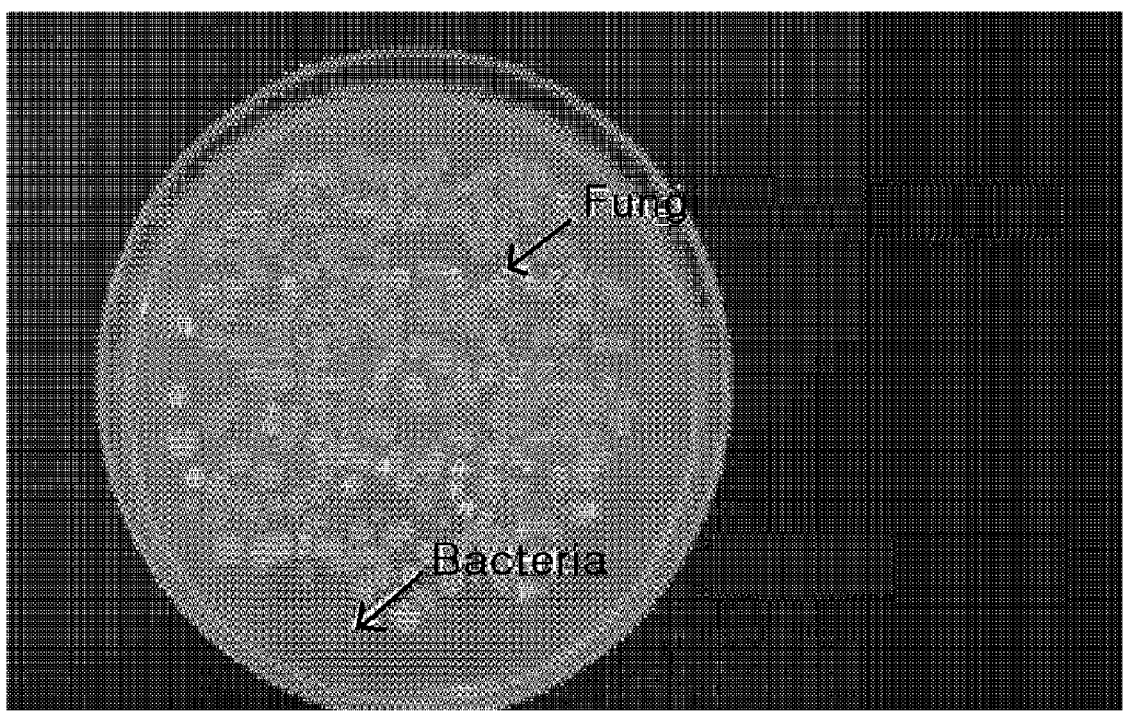
FIG. 28 shows the growth of bacteria and fungi obtained from indoor dust.

Extracellular vesicles found in indoor air may be produced by various bacteria or fungi that live in indoor dust. Dust was collected from bedclothes using a vacuum cleaner. The dust arrested by the filter of the vacuum cleaner was transferred to a clean vial and weighed. Five grams of the dust was solubilized at 4° C. for 12 hours in 200 mL of PBS in a beaker. Large-size substances were filtered out through gauze. This dust solution was diluted ¹/₁₀ and the dilution was spread over plates containing the culture medium. Incubation visualized the appearance of bacteria and fungi. As seen in FIG. 28, various bacteria and fungi live in indoor dust.

Figure 29:
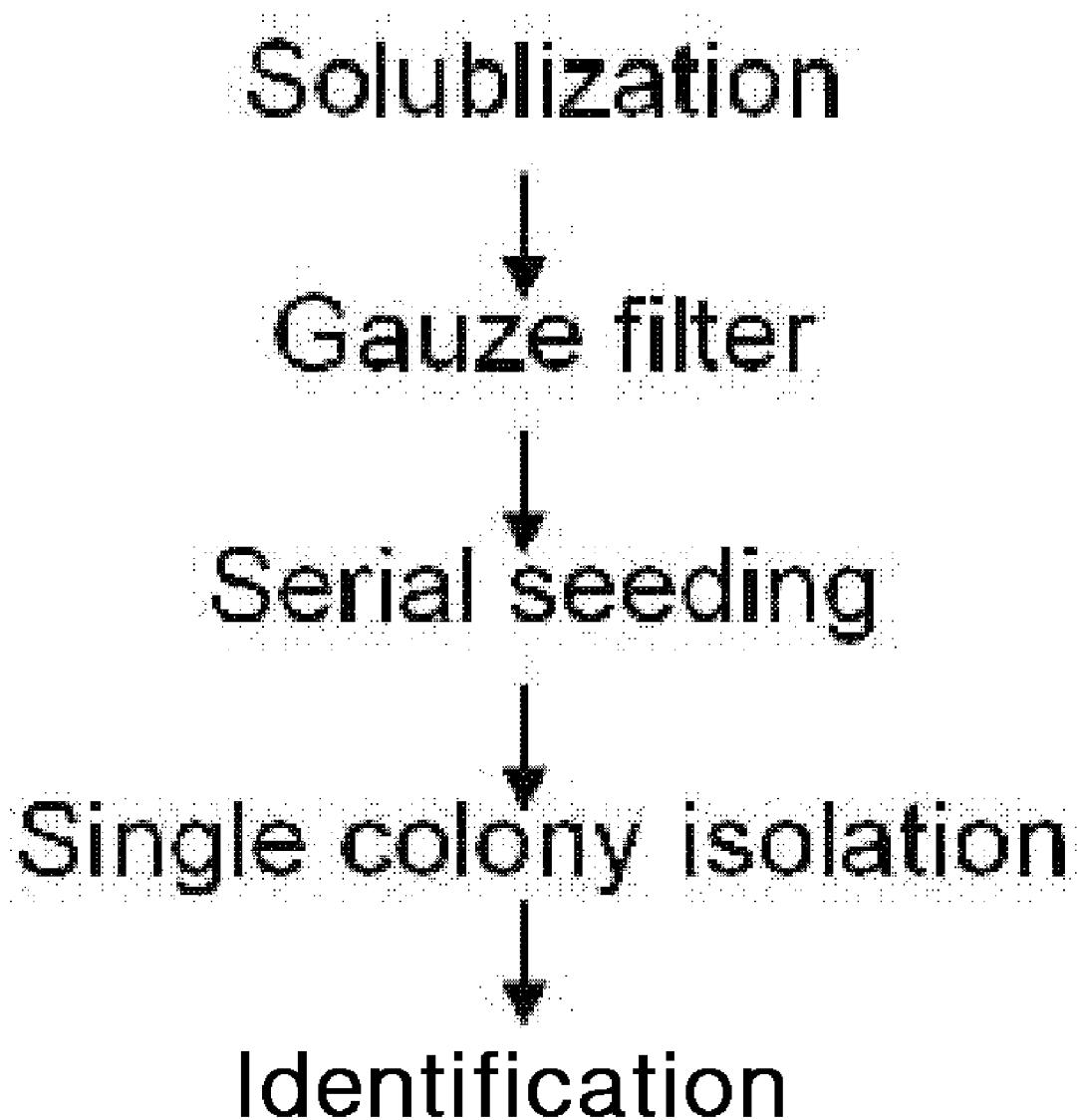
FIG. 29 shows a process of isolating bacteria from indoor dust.

Then, an experiment was performed to isolate and identify the bacteria living in indoor dust. FIG. 29 shows a process of isolating bacteria from indoor dust. Dust, after being harvested from bedclothes, was solubilized as described in Example 1 and substances of large size were removed using a gauze filter. The dust solution was diluted ¹/₁₀ and spread over plates containing a culture medium. Incubation under predetermined conditions visualized the growth of various colonies which are different in size and color from each other. Each colony was inoculated into 3 mL of nutrition broth in a test tube and cultured at 37° C. The bacteria were identified using VITEK®, an automated system for identifying microbes using a biochemical method. As a result, the Gram-positive bacteria *Staphylococcus aureus*, and *Staphylococcus hominis* were identified.

Hence, it can be seen that Gram positive bacteria present in indoor dust are among the organisms secreting extracellular vesicles.

Example 16

In Vitro Immune Responses Induced by *Staphylococcus aureus*-Derived Extracellular Vesicles Recently, the present inventors first reported the secretion of extracellular vesicles from the Gram-positive bacteria *Staphylococcus aureus*. Extracellular vesicles were isolated from a culture of *S. aureus* as described in Example 1 and examined for their pathogenicity for respiratory diseases.

In detail, *S. aureus* was inoculated into 3 ml of LB broth in a test tube and cultured at 37° C. for 6 hour. From the culture, 5 mL was transferred to 500 ml of nutrient broth in a 2 L-Erlenmeyer flask and incubated at 37° C. for 4 hours to an O.D. (600 nm) of 1.0. All the culture was equally distributed to 500 mL-ultracentrifuge tubes and spun at 4° C. and 10,000×g for 20 min. The supernatant devoid of cells was passed once through a membrane filter with a pore size of 0.45 μm, and the filtrate was 25-fold concentrated using the Quixstand system with 100 kDa cutoff. After one passage of the concentrate through a membrane filter with a pore size of 0.22 μm, the resulting filtrate was ultra-centrifuged at 4° C. and 150,000×g for 3 hours in 70 mL-ultracentrifuge tubes. The pellets thus formed were re-suspended in PBS to separate extracellular vesicles derived from *S. aureus*.

Figure 30:
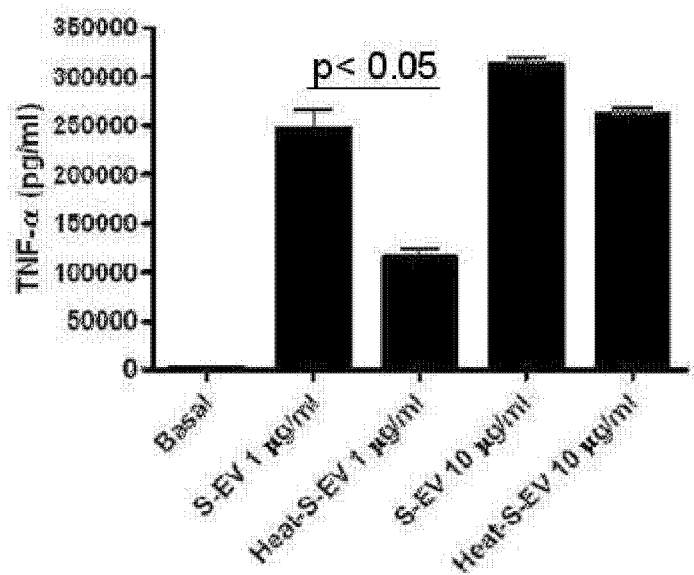
FIG. 30 shows the induction of in vitro innate immune responses upon the treatment of mouse macrophages with *Staphylococcus aureus*-derived extracellular vesicles (S-EV) and thermally treated vesicles, as analyzed by the levels of TNF-α and IL-6.
Figure 30:
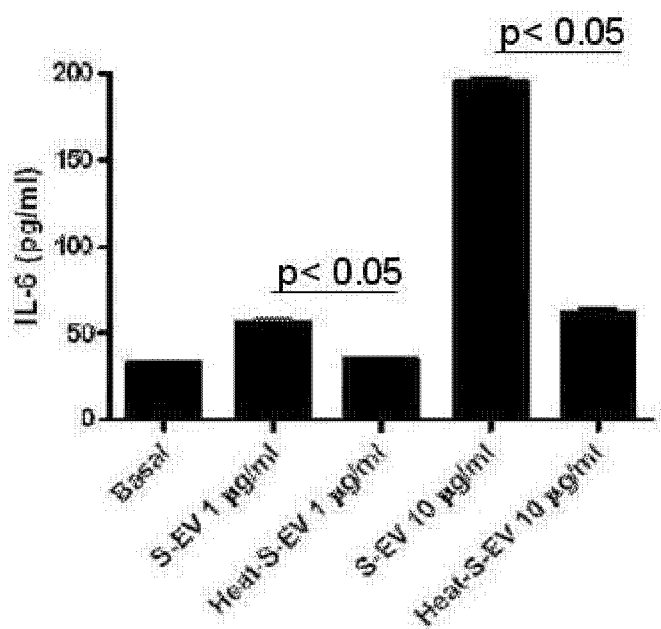

For use in the in vitro testing of the immune responses to *S. aureus*-derived extracellular vesicles, mouse macrophages (RAW264.7) were seeded at a density of $1 \times 10^5$ cells/well into 24-well plates, grown for 24 hours and then washed with PBS to remove FBS (fetal bovine serum). The macrophages in DMEM treated with 1 and 10 μg/ml of *S. aureus*-derived extracellular vesicles were used as controls. For test groups, *S. aureus*-derived extracellular vesicles that had been boiled at 100° C. for 20 min were used. After the cells were incubated with the extracellular vesicles for 15 hours, the culture media were harvested and centrifuged at 4° C. and 800×g for 10 min. Levels of cytokines in the supernatants were determined using ELISA (enzyme linked immunosorbent assay). FIG. 30 is of graphs showing the expression levels of the representative inflammatory cytokines TNF-α and IL-6.

As can be seen in FIG. 30, the level of TNF-α was reduced by half in the group treated with 1 μg/ml of the thermally treated extracellular vesicles (Heat-S-EV), but were not significantly changed upon treatment with 10 μg/ml. In contrast, the level of IL-6 was significantly decreased in the groups treated with thermally treated *S. aureus*-derived extracellular vesicles (Heat-S-EV), irrespective of their concentrations.

From these results, it is understood that a protein or heat-susceptible component in *S. aureus*-derived extracellular vesicles plays an important role in IL-6-mediated inflammation.

Example 17

Figure 31:
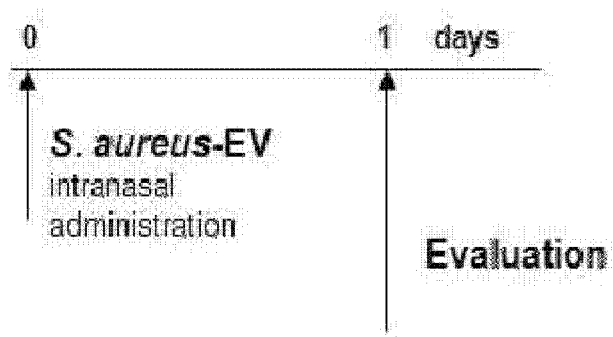
FIG. 31 is a diagram showing a protocol for evaluating the induction of in vivo innate immune responses using *Staphylococcus aureus*-derived extracellular vesicles.

In Vivo Innate Immune Response and Lung Inflammation Induced by *S. aureus*-Derived Extracellular Vesicles To evaluate the in vivo immune responses induced by *S. aureus*-derived extracellular vesicles, C57BL/6 mice (6 weeks old, female, three in each group) were administered via the airway with 1 and 10 μg of *S. aureus*-derived extracellular vesicles in PBS for test groups and with PBS alone for a control. On the next day after the injection of the extracellular vesicles, early lung inflammation and the level of IL-6 were examined (protocol of FIG. 31).

Figure 32:
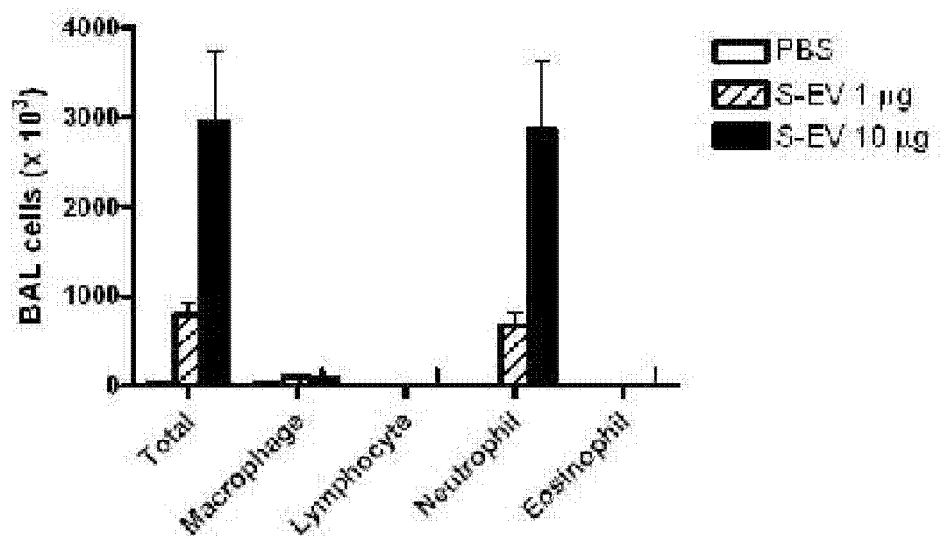
FIG. 32 is a graph showing inflammatory cell counts of BAL fluid after *Staphylococcus aureus*-derived extracellular vesicles (S-EV) are intranasally administered according to the protocol of FIG. 31.

FIG. 32 is a graph showing counts of inflammatory cells in BAL fluid after administration with *S. aureus*-derived extracellular vesicles (S-EV) via the airway. The inflammatory cell count of BAL fluid increased in a dose-dependent manner, with the preponderance of inflammatory cells being neutrophils.

Figure 33:
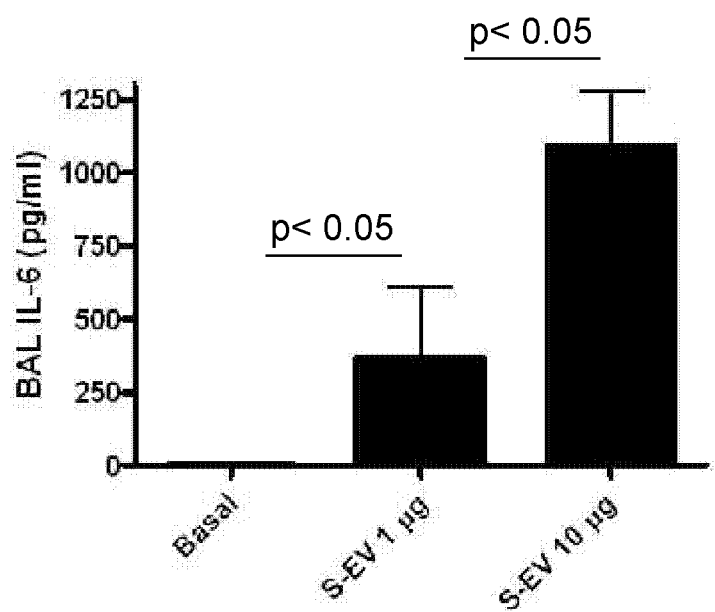
FIG. 33 is a graph showing levels of IL-6 in BAL fluid after *Staphylococcus aureus*-derived extracellular vesicles (S-EV) are intranasally administered according to the protocol of FIG. 31.

Also, the level of IL-6, essential to generate a Th17-mediated immune response, in BAL fluid was determined using ELISA. As shown in FIG. 33, *S. aureus*-derived extracellular vesicles (S-EV) increased the expression level of IL-6 in a dose-dependent manner.

From these results, it is apparent that the inhalation of *S. aureus*-derived extracellular vesicles causes neutrophilic lung inflammation and stimulates the production of IL-6, a key player in the Th17-mediated immune response.

Example 18

Role of Protein or Heat-Susceptible Component in Innate Immune Responses Induced by *S. aureus*-Derived Extracellular Vesicles In addition to the in vitro experiment of Example 16, the role of proteins in *S. aureus*-derived extracellular vesicles in the generation of an innate immune response was examined in vivo.

Figure 34:
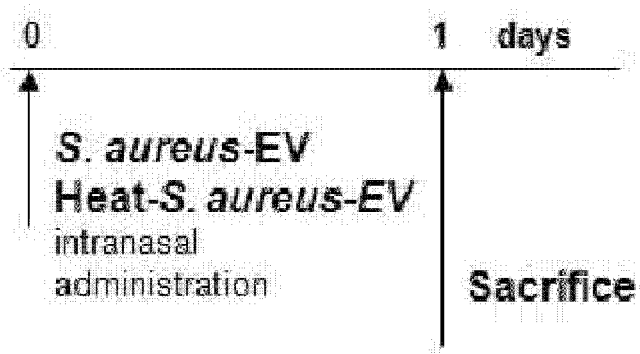
FIG. 34 is a diagram showing a protocol for evaluating the role of vesicular proteins or heat resistant components in the induction of immune responses using *Staphylococcus aureus*-derived extracellular vesicles.

C57BL/6 mice (6 weeks old, female, three in each group) were administered through the airway with 1 and 10 μg of extracellular vesicles serving as a control. After being boiled at 100° C. for 20 min, the extracellular vesicles were administered to a test group. On the next day after the administration, early lung inflammation and the level of IL-6 in the mice were examined (protocol of FIG. 34).

Figure 35:
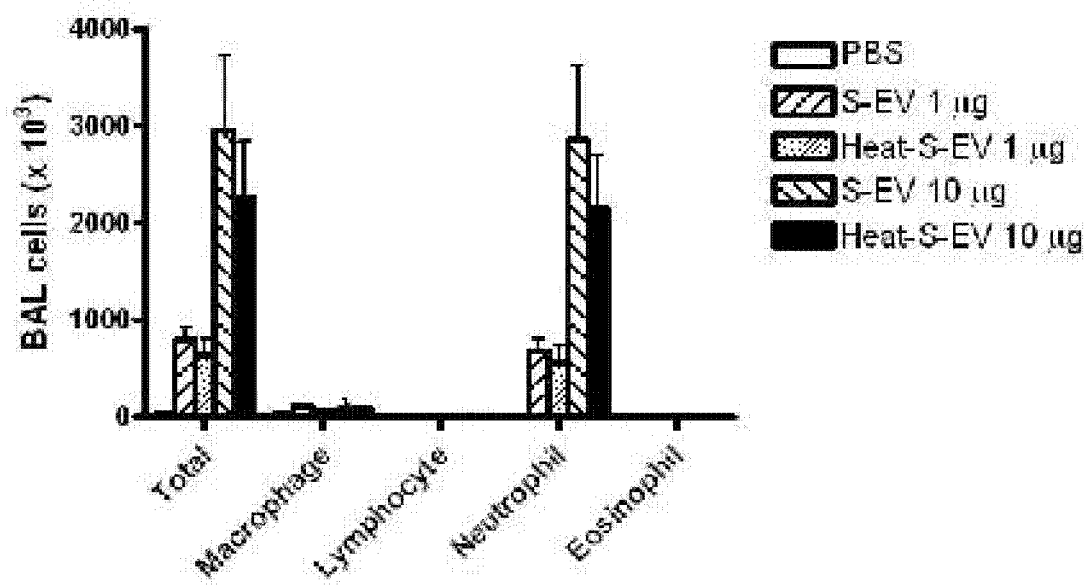
FIG. 35 is a graph showing the inflammatory cell count of BAL fluid after thermally treated *Staphylococcus aureus*-derived extracellular vesicles (S-EV) were intranasally administered according to the protocol of FIG. 34.

FIG. 35 is a graph showing inflammation in BAL fluid after the administration of *S. aureus-extracellular* vesicles through the airway. There was no significant difference in inflammation (inflammatory cell count of BAL fluid) between the group administered with 10 μg of thermally treated extracellular vesicles (Heat-S-EV 10 μg) and the control (S-EV 10 μg).

Figure 36:
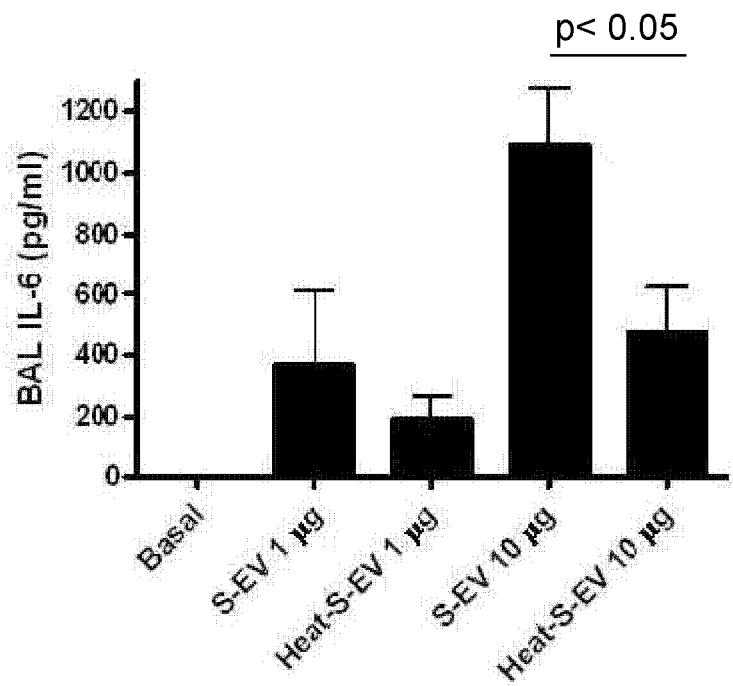
FIG. 36 is a graph showing levels of IL-6 in BAL fluid after thermally treated *Staphylococcus aureus*-derived extracellular vesicles (S-EV) were intranasally administered according to the protocol of FIG. 34.

FIG. 36 is a graph showing the level of IL-6 in BAL fluid as measured by ELISA. Unlike lung inflammation, as shown in the graph, the level of IL-6 was significantly reduced in the groups administered with thermally treated *S. aureus*-derived extracellular vesicles (1 μg, 10 μg), compared to the control.

Hence, it was confirmed that a protein or heat-susceptible component of *S. aureus*-derived extracellular vesicles plays an important role in the induction of an IL-6-mediated immune response and inflammatory respiratory disease.

Example 19

Immunological Properties of *E. coli*-Derived Extracellular Vesicles

*E. coli*-derived extracellular vesicles prepared in Example 8 were intraperitoneally injected into C57BL/6 mice (male, 6 weeks old, 10 in each group) at a dose of 1 μg three times over three weeks at regular intervals of one week. Blood samples were taken 6 and 24 hours and 7 days after each injection and used to examine antibodies specific for the extracellular vesicles. After being diluted 1:500 in 1% BSA/PBS, the mouse serum was added to black 96-well plates coated with 200 ng of *E. coli*-derived vesicles per well. After incubation for 2 hours, an observation was made of the immunological change with a peroxidase-conjugated anti-mouse antibody.

Figure 37:
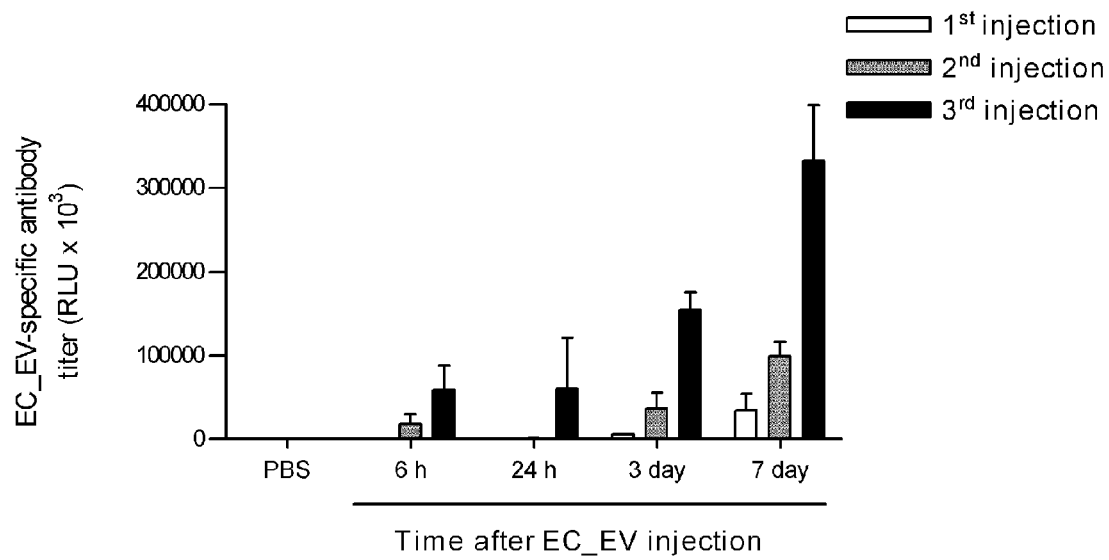
FIG. 37 is a graph showing the levels of vesicle-specific antibodies measured in the course of three intraperitoneal injections of 1 μg of *E. coli*-derived extracellular vesicles (EC_EV) at regular intervals of one week.

FIG. 37 is a graph in which levels of *E. coli*-derived extracellular vesicle (EC_EV)-specific antibodies in the mouse blood are plotted against time. The extracellular vesicle-specific antibodies started to form 7 days after the first injection of extracellular vesicles and was amplified by the second and the third injection of the extracellular vesicles, with a peak at 7 days after the third injection.

Seven days after the three injections of *E. coli*-derived extracellular vesicles (EC_EV) were completed, splenocytes were isolated from the mice. The splenocytes ($2\times10^4$) were incubated for 72 hours with 100 ng of *E. coli*-derived extracellular vesicles, followed by ELISA to quantitatively analyze IFN-γ, IL-17 and IL-4, all secreted from splenocytes.

Figure 38:
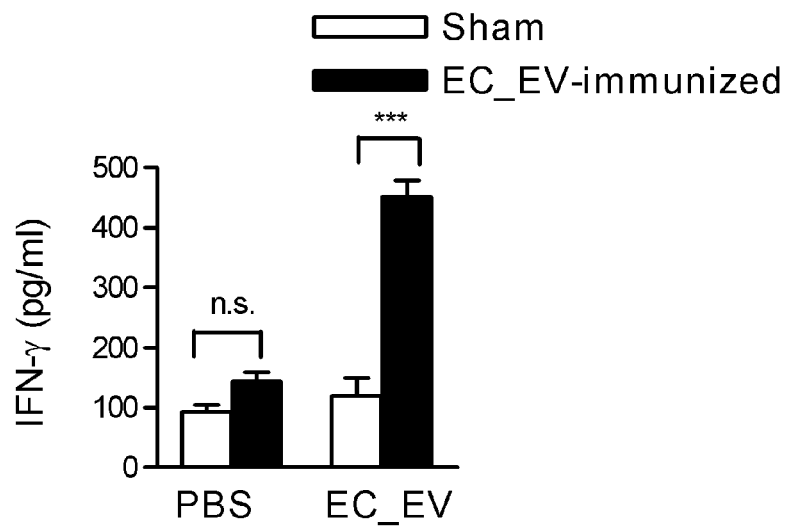
FIG. 38 shows the levels of IFN-γ secreted from mouse splenocytes upon ex vivo treatment with *E. coli*-derived extracellular vesicles after the mice were immunized with the *E. coli*-derived extracellular vesicle (EC_EV) vaccine.

FIG. 38 shows the levels of IFN-γ secreted from mouse splenocytes upon treatment with *E. coli*-derived extracellular vesicles (EC_EV). As can be seen, a higher level of IFN-γ was secreted from the splenocytes of the. *E. coli*-derived extracellular vesicle-immunized group, compared to the sham group.

Figure 39:
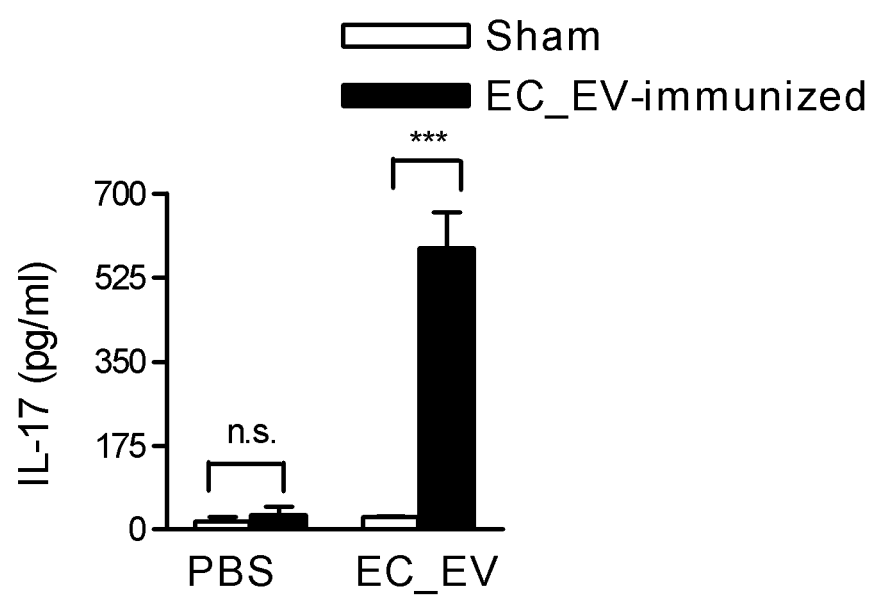
FIG. 39 shows the levels of IL-17 secreted from mouse splenocytes upon ex vivo treatment with *E. coli*-derived extracellular vesicles after the mice were immunized with the *E. coli*-derived extracellular vesicle (EC_EV) vaccine.

FIG. 39 shows the levels of IL-17 secreted from mouse splenocytes upon treatment with *E. coli*-derived extracellular vesicles (EC_EV). As can be seen, a higher level of IL-17 was secreted from the splenocytes of the. *E. coli*-derived extracellular vesicle-immunized group, compared to the sham group.

From these results, it is confirmed that immunization with *E. coli*-derived extracellular vesicles activates the defense system against bacterial infection, including the antibody production of B cells and the T cell immune response. Particularly, as for the T cell immune response, the Th1 immune response responsible for IFN-γ secretion and the Th17 immune response responsible for IL-17 secretion, both playing an important role in defense against bacterial infection, were effectively activated by immunization with *E. coli*-derived extracellular vesicles.

Example 20

Efficacy of *E. coli*-Derived Extracellular Vesicle Vaccine Against *E. coli* Infection-Induced Sepsis For use in evaluating the efficacy of *E. coli*-derived extracellular vesicle vaccines, *E. coli* infection-induced animal models of sepsis were established. *E. coli* was intraperitoneally injected at a dose of $1\times10^6$, $1\times10^8$ and $1\times10^{10}$ CFU into C57BL/6 mice (male, 6 weeks old, 10 in each group) the survival of which were then monitored at regular intervals of 8 hours for 5 days.

Figure 40:
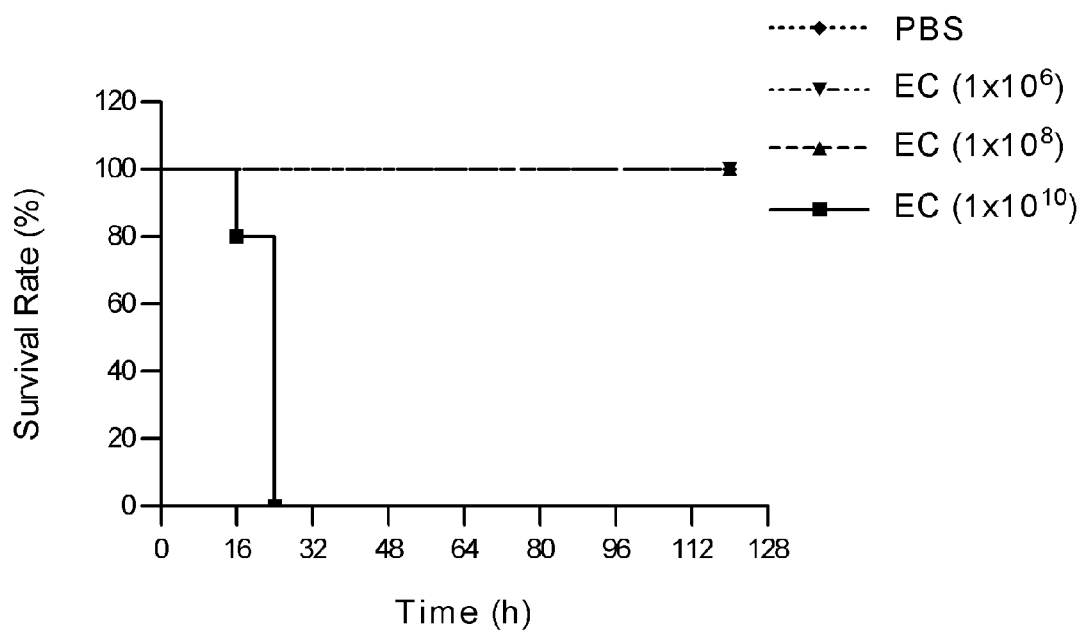
FIG. 40 shows survival rates of the mice in which sepsis was induced by the intraperitoneal injection of *E. coli* (EC).

FIG. 40 shows survival rates of the mice infected with *E. coli* (EC). As shown in this graph, mice were dead within 24 hours after the injection of *E. coli* at a dose of $1\times10^{10}$ CFU, but did not die with injections of $1\times10^6$ or $1\times10^8$ CFU of *E. coli*.

Figure 41:
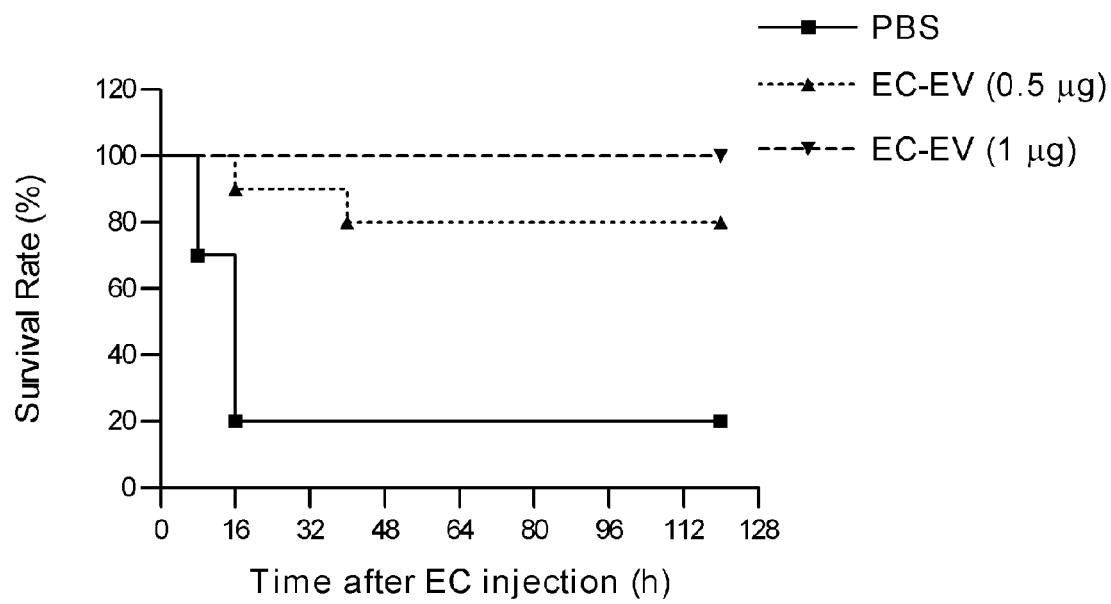
FIG. 41 shows the efficacy of the *E. coli*-derived extracellular vesicle (EC_EV) vaccines against the *E. coli* (EC) infection-induced sepsis.

*E. coli*-derived extracellular vesicles were intraperitoneally injected once a week for three weeks at a dose of 0.5 and 1 μg to C57BL/6 mice (male, 6 weeks old, 10 in each group) according to the method of Example 19. Seven days after the three immunizations of the *E. coli*-derived extracellular vesicles, the mice were intraperitoneally challenged with $1\times10^{10}$ CFU of *E. coli* and their survival rates were monitored at regular intervals of 8 hours for 5 days. FIG. 41 shows the efficacy of the *E. coli*-derived extracellular vesicle vaccines against the *E. coli* infection-induced sepsis established above. Five days after the challenge, the mice were observed to survive at a rate of 20% when not immunized with the *E. coli*-derived extracellular vesicles, but the survival rate was increased to 80-100% in the mice immunized with the *E. coli*-derived extracellular vesicles.

As described above, *E. coli*-derived extracellular vesicles were intraperitoneally injected at a dose of 1 μg once a week for three weeks to mice which were then intraperitoneally challenged with $1\times10^{10}$ CFU of *E. coli*. Six hours later, *E. coli* in ascites and blood were counted and the results are depicted in FIG. 42.

Figure 42:
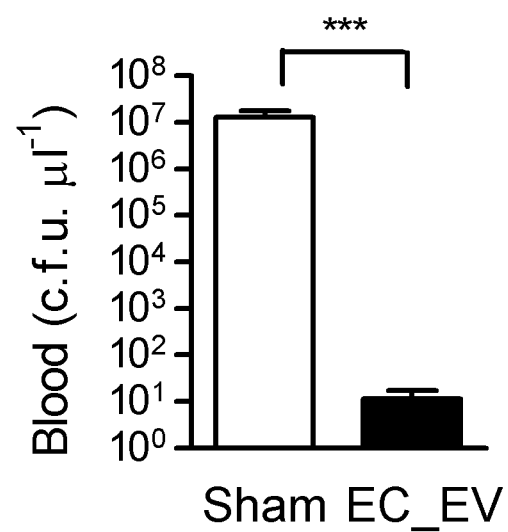
FIG. 42 shows *E. coli* CFU in mice immunized with and without *E. coli*-derived extracellular vesicles (EC_EV) upon the intraperitoneal injection of *E. coli* (EC).

FIG. 42 shows *E. coli* CFU in mice challenged with and without *E. coli*-derived extracellular vesicles. After an *E. coli* infection, a significantly smaller number of *E. coli* was detected in the blood from the mice immunized with *E. coli*-derived extracellular vesicles, compared to those not immunized with *E. coli*-derived extracellular vesicles.

This data demonstrates that extracellular vesicles derived from *E. coli* can be used as a vaccine for effectively preventing *E. coli* infections.

Example 21

Efficacy of *E. coli*-Derived Extracellular Vesicle Vaccines Against *E. coli*-Derived Extracellular Vesicle-Induced Inflammation In order to evaluate the efficacy of the vesicular vaccine against the inflammation induced by *E. coli*-derived extracellular vesicles, C57BL/6 mice (male, 6 weeks old, 5 in each group) were immunized by intraperitoneal injections of 1 µg of *E. coli*-derived extracellular vesicles once a week for three weeks according to the method of Example 19. When sepsis was induced by intraperitoneal injection of *E. coli*-derived extracellular vesicles, the level of inflammatory cytokines in the serum was measured.

Figure 43:
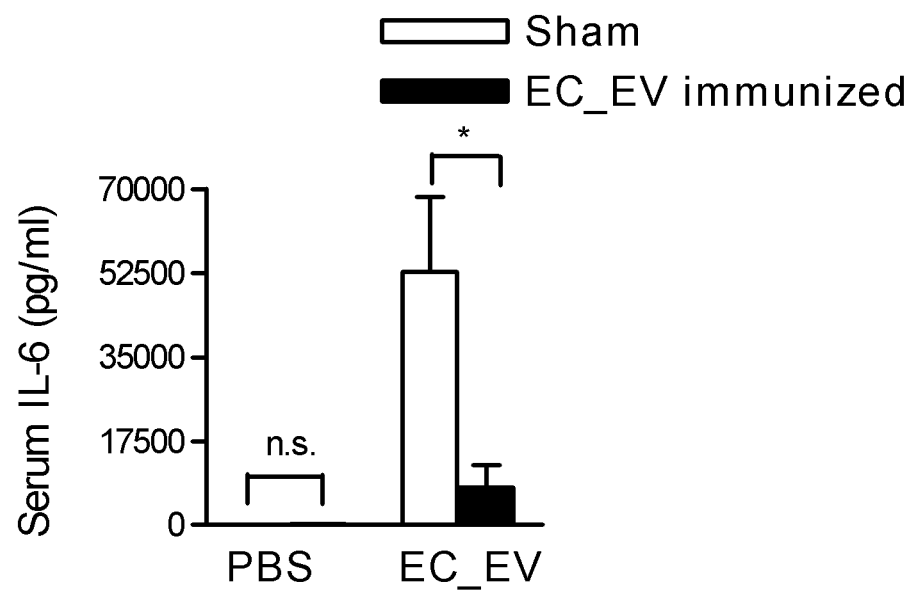
FIG. 43 shows blood IL-6 levels measured 6 hours after three intraperitoneal injections of *E. coli*-derived extracellular vesicles (5 μg) into mice immunized and not immunized with *E. coli*-derived extracellular vesicles (EC_EV).

FIG. 43 shows the levels of IL-6, a cytokine inducing Th17-mediated immune responses, in the sera of mice as measured 6 hours after three injections of a high dose of *E. coli*-derived extracellular vesicles (5 µg). As can be seen, blood IL-6 levels were significantly decreased in the mice immunized with *E. coli*-derived extracellular vesicles, as compared to non-immunized mice.

Taken together, the data obtained above indicate that *E. coli*-derived extracellular vesicles can be used as an effective vaccine against inflammation caused by *E. coli*-derived extracellular vesicles.

Although the preferred embodiments of the present invention have been disclosed for illustrative purposes, those skilled in the art will appreciate that various modifications, additions and substitutions are possible, without departing from the scope and spirit of the invention as disclosed in the accompanying claims Industrial Applicability The indoor air-derived extracellular vesicles of the present invention can be used in diagnosing, preventing and/or treating inflammatory respiratory diseases. In detail, animal models of respiratory diseases can be established by administering the indoor air-derived extracellular vesicles to animals and can be used to screen and discover drug candidates preventive or therapeutic of respiratory diseases. Also, the present invention allows the diagnosis of exact pathogenic factors responsible for the onset of respiratory diseases such as severe asthma, chronic obstructive pulmonary disease, lung cancer, etc., and can be applied to the development of vaccines against the diseases.

The invention claimed is:

1. A method of determining quality of indoor air by determining if indoor air contains a material originating from at least one of pre-identified pathogenic microorganisms, the method comprising:
    collecting an indoor dust sample;
    processing the indoor dust sample to obtain a concentrated population of extracellular vesicles contained therein;
    mixing at least part of the concentrated population with a primer that has a sequence complementary to a first genetic substance of a first one of the pre-identified pathogenic microorganisms such that if the concentrated population contains extracellular vesicles of the first pre-identified pathogenic microorganism, the primer would recognize the first genetic substance of the first pre-identified pathogenic microorganism;
    subjecting the mixture to amplification of at least one specific nucleotide sequence that is recognized by the primer;
    processing the amplification product to determine if the at least one specific nucleotide sequence has been amplified therein; and
    once determined that the at least one specific nucleotide sequence has been amplified, determining that the indoor air contains materials from the first pre-identified pathogenic microorganism.

2. A method of determining quality of indoor air by determining if indoor air contains a material originating from at least one of pre-identified pathogenic microorganisms, the method comprising:
    collecting an indoor dust sample;
    processing the indoor dust sample to obtain a concentrated population of extracellular vesicles contained therein;
    mixing at least part of the concentrated population with an antibody that has specificity to a first protein of a first one of the pre-identified pathogenic microorganisms such that if the concentrated population contains extracellular vesicles of the first pre-identified pathogenic microorganism, the antibody would bind with the first protein of the first pre-identified pathogenic microorganism;
    subsequently, processing to determine if the antibody has bound with the first protein; and
    once determined that the antibody has bound with the first protein, determining that the indoor air contains materials from the first pre-identified pathogenic microorganism.

3. A method of determining quality of indoor air by determining if indoor air contains a material originating from at least one of pre-identified pathogenic microorganisms, the method comprising:
    collecting an indoor dust sample;
    processing the indoor dust sample to obtain a concentrated population of extracellular vesicles contained therein;
    contacting at least part of the concentrated population with animal cells such that if the concentrated population contains extracellular vesicles of the first pre-identified pathogenic microorganism, the extracellular vesicles would induce an immune response in the animal cells, wherein the animal cells are pre-cultured in vitro or part of a live animal;
    subsequently, processing to determine if an immune response has occurred in the animal cells; and
    once determined that an immune response has occurred in the animal cells, determining that the indoor air contains materials from the first pre-identified pathogenic microorganism.

4. The method according to claim 3, wherein said at least one of pre-identified pathogenic microorganisms belongs to one or more genus selected from the group consisting of *Staphylococcus, Micrococcus, Enterococcus, Pseudomonas, Streptomycetes*, and *Corinebacterium*.

5. The method according to claim 3, wherein said at least one of pre-identified pathogenic microorganisms is selected from the group consisting of *Staphylococcus aureus, Staphylococcus hominis, Micrococcus lylae, Enterococcus faecalis, Pseudomonas stutzeri, Pseudomonas luteola*, and *Escherichia coli*.

6. The method according to claim 3, the immune response is selected from the group consisting of Th1 immune response and Th17 immune response.

7. The method according to claim 1, wherein said at least one of pre-identified pathogenic microorganisms belongs to one or more genus selected from the group consisting of

*Staphylococcus, Micrococcus, Enterococcus, Pseudomonas, Streptomycetes*, and *Corinebacterium*.

8. The method according to claim 1, wherein said at least one of pre-identified pathogenic microorganisms is selected from the group consisting of *Staphylococcus aureus, Staphylococcus hominis, Micrococcus lylae, Enterococcus faecalis, Pseudomonas stutzeri, Pseudomonas luteola*, and *Escherichia coli*.

9. The method according to claim 2, wherein said at least one of pre-identified pathogenic microorganisms belongs to one or more genus selected from the group consisting of *Staphylococcus, Micrococcus, Enterococcus, Pseudomonas, Streptomycetes*, and *Corinebacterium*.

10. The method according to claim 2, wherein said at least one of pre-identified pathogenic microorganisms is selected from the group consisting of *Staphylococcus aureus, Staphylococcus hominis, Micrococcus lylae, Enterococcus faecalis, Pseudomonas stutzeri, Pseudomonas luteola*, and *Escherichia coli*.

\* \* \* \* \*